United States Patent [19]

Steele et al.

[11] Patent Number: 5,389,518

[45] Date of Patent: Feb. 14, 1995

[54] MONOCLONAL ANTIBODIES DIRECTED AGAINST VITRONECTIN AND FIBRONECTIN, AND USES THEREOF

[75] Inventors: John G. Steele, North Rocks; Patricia A. Underwood, Annandale, both of Australia

[73] Assignee: Commonwealth Scientific and Industrial Research Organisation, Act, Australia

[21] Appl. No.: 730,931

[22] PCT Filed: Feb. 5, 1990

[86] PCT No.: PCT/AU90/00039

§ 371 Date: Aug. 1, 1991

§ 102(e) Date: Aug. 1, 1991

[87] PCT Pub. No.: WO90/08834

PCT Pub. Date: Aug. 9, 1990

[30] Foreign Application Priority Data

Feb. 3, 1989 [AU] Australia .............................. PJ2529

[51] Int. Cl.$^6$ .......................................... G01N 33/554
[52] U.S. Cl. .................... 435/7.21; 435/7.9; 435/7.92; 435/70.21; 435/240.23; 435/240.27; 435/204.241; 435/240.243; 436/524; 436/528; 436/531; 436/825; 530/388.2; 530/391.1
[58] Field of Search ............ 435/7.21, 240.23, 240.241, 435/240.243, 7.92, 7.9, 7.91, 7.95, 7.1, 7.2; 436/824, 825, 518, 524, 528, 531; 530/388.1, 391.1, 388.2

[56] References Cited

U.S. PATENT DOCUMENTS 4,059,685 11/1977 Johnson ................................. 424/12
4,376,110 3/1983 David et al. ........................ 436/513
4,746,604 5/1988 Mowshowitz ......................... 435/7
4,828,563 5/1989 Müller-Lierheim .................. 623/16

FOREIGN PATENT DOCUMENTS

WO8801279 2/1988 WIPO .

OTHER PUBLICATIONS

Harrison et al., "Adhesive responses of fibroblast and neuroblastoma cells to substrata coated with polyvalent or monoclonal antibody to fibronectin," *Chem. Abs.*, 99, No. 85807k (1983).
Schoen, R. et al., *Monoclonal Antibodies Against Human Fibronectin Which Inhibit Cell Attachment*, Hybridoma, vol. 1, No. 2, 1982 pp. 99–106 New York, US.
Kajikawa, H. et al., *Characterization of Monoclonal Anitbodies Against Bovine Plasma Fibronectin*, Zoological Science, vol. 5, No. 6, Dec. 1988, p. 1326, Tokyo, JP Abstract Only.
Hayman, E. et al., *Serum Spreading Factor–virtonectin–is present at the Cell Surface and in Tissues*, Proceedings of the National Academy of Sciences of the United States of America, vol. 80, No. 13, Jul. 1983, pp. 4003–4007, Washington, D.C., US.
Schakenraad, J. et al., *Kinetics of Cell Spreading on Protein Precoated Substrata: A Study of Interacial Aspects*, BIomaterials, vol. 10, No. 1, Jan. 1989, pp. 43–50, Guildford, Surrey, GB.
Salonen et al. *J. Immunol. Methods* V. 72: (1984) pp. 145–156.
Hashida and Ishikawa *Analytical Letters* vol. 18 (B9) (1985) pp. 1143–1155.
Lydon and Foulger *Biomaterials* vol. 9 (1988) pp. 525–527.
Cell Structure and Function, vol. 13, issued Mar. 1988, Masako Izumi, et al, 'Identification of the Collagen-Binding Domain of Vitronectin Using Monoclonal Antibodies', pp. 218–219.
Thrombosis and Haemostasis, Vo. 60, No. 3, issued Apr. 1988, Perumal Thiagarajan and Kathleen Kelly, 'Interaction of Thrombin-Stimulated Platelets and Vitronectin (S–Protein of Complement) Substrate: Inhibition by a Monoclonal Antibody to Glycoprotein IIb–IIIa complex'.

Primary Examiner—Carol A. Spiegel
Attorney, Agent, or Firm—Christie, Parker & Hale

[57] ABSTRACT

The present invention provides monoclonal antibodies directed against specific domains of fibronectin and vitronectin. These monoclonals may be used in the production of the biomaterial and devices for use in in vitro cell culture. The present invention also provides an efficient method for extracting vitronectin from bovine serum or plasma using monoclonal antibodies and methods for analyzing biological samples for the presence of adhesive glycoproteins or fragments thereof.

12 Claims, 13 Drawing Sheets

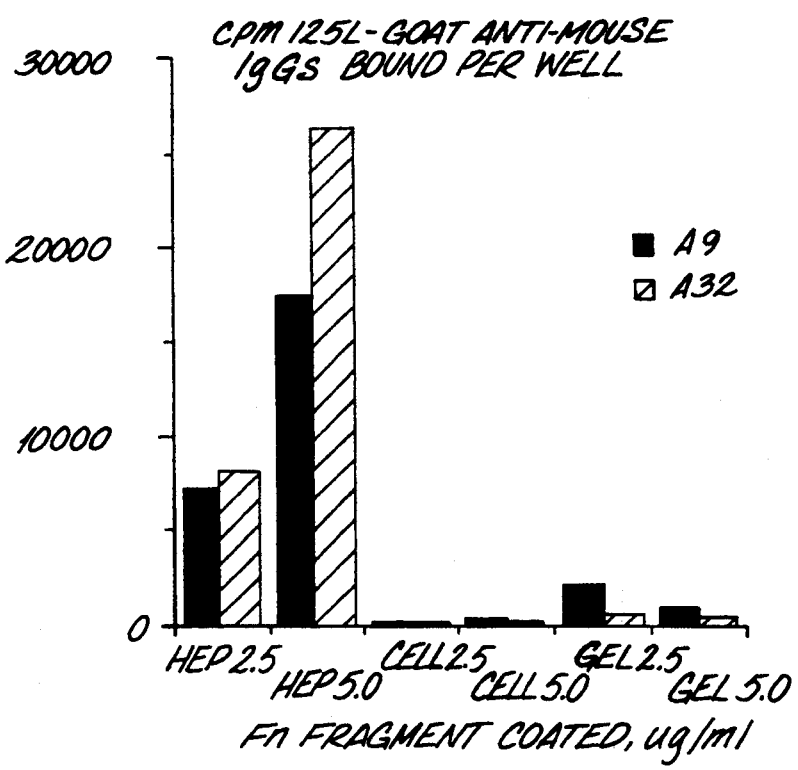
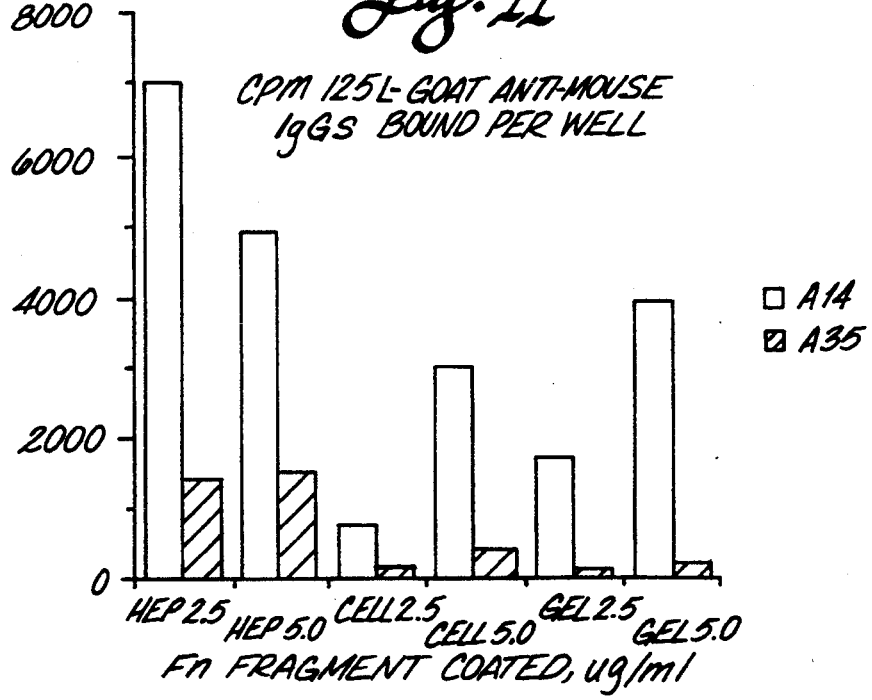

MONOCLONAL ANTIBODIES DIRECTED AGAINST VITRONECTIN AND FIBRONECTIN, AND USES THEREOF

The present invention in general relates to the involvement of adhesive glycoproteins, such as vitronectin and fibronectin in the attachment and growth of animal cells on non-biological surfaces, such as polymeric plastics, metals, ceramics etc. More particularly, the present invention relates to monoclonal antibodies directed against vitronectin and fibronectin and to the use of such monoclonal antibodies in the production of a biomaterial and a device for use in in vitro cell culture. The present invention also relates to a method for analysing biological samples for the presence of adhesive glycoproteins or fragments thereof and to a method of extracting vitronectin from bovine serum or plasma, to vitronectin so produced, and to a device used in the extraction method.

One of the major difficulties presently encountered in the preparation of biomaterials for certain applications is that of ensuring cellular attachment to the biomaterial. Cellular attachment to a number of polymeric materials used for biomaterials, such as teflon, is dependent on adsorption of serum or cellular glycoproteins which are adhesive for cells, however, adsorption to these surfaces is low and non-specific. It is believed that the design of a biomaterial surface would be advantaged if glycoproteins could be specifically bound and held with higher affinity by the biomaterial surface. It would also be of advantage if the glycoproteins adsorbed onto the biomaterial surface were derived from the plasma or serum of the patient, and that the plasma or serum could be used without the requirement to initially purify the adhesive glycoproteins from the plasma or serum.

Adhesive glycoproteins such as fibronectin or vitronectin are multidomain proteins, each domain having a biological activity, and so the biological activity of a surface that has adsorbed such a glycoprotein is dependent upon the way in which the domain or domains of the glycoprotein are presented. It is believed that the ability to modify the biological activity of a surface to which adhesive glycoproteins are adsorbed by choosing the orientation in which the adhesive glycoproteins are bound would also be advantageous.

As stated previously the present invention also relates to a method of extracting vitronectin and to a device for use in such a method. There are a number of prior art methods for producing vitronectin and these methods, together with the drawbacks encountered by these methods are discussed in European patent application No. 0292663. As is stated in European patent application No. 0292663 it is known to extract vitronectin from human plasma or serum using anti-human vitronectin monoclonal antibodies. However, such methods have generally resulted in a poor recovery in the order of about 10 to 20%. The present invention enables the extraction of vitronectin from bovine plasma or serum with a recovery in the order of 90%.

The present inventors have produced two hybridoma cell lines which produce monoclonal antibodies each of which is reactive with a different epitope of bovine vitronectin. Accordingly, in a first aspect the present invention consists in a monoclonal antibody reactive with vitronectin in a manner such that when the monoclonal antibody is bound to vitronectin, the vitronectin retains its cell binding activity. The present invention further consists in a hybridoma cell line producing such a monoclonal antibody.

This monoclonal antibody has been designated A27, and the hybridomas cell line producing monoclonal antibody A27 has been designated CM 30/23 D2/G4. This hybridoma cell line has been deposited with the European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom, on 12 Jan. 1989 and accorded accession number 89011102.

In a second aspect the present invention consists in a monoclonal antibody reactive against bovine vitronectin in a manner such that when the monoclonal antibody is bound to vitronectin, the cell binding ability of vitronectin is lost. This aspect of the present invention further consists in a hybridoma cell line producing such a monoclonal antibody.

This monoclonal antibody has been designated A18, and the hybridoma cell line producing monoclonal antibody A18 has been designated CM 26/12 3D11. This hybridoma cell line has been deposited with the European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom, on 12 Jan. 1989 and accorded accession number 89011103.

The present inventors have also produced a number of monoclonal antibodies reactive with fibronectin. A number of these monoclonal antibodies react with fibronectin in a manner such that the cell binding ability of fibronectin is lost, whilst others bind to fibronectin in a manner such that the cell binding activity of fibronectin is retained.

In particular monoclonal antibodies designated A9 and A35 have been isolated. These monoclonal antibodies are characterised in that they react with bovine fibronectin and cross react with human fibronectin. Both monoclonal antibodies are reactive with fibronectin in a manner such that when the monoclonal antibody is bound to fibronectin the fibronectin retains its cell binding activity. Both of these monoclonal antibodies bind to the heparin binding region of the fibronectin molecule at the carboxy terminus.

In a third aspect the present invention consists in a biomaterial comprising a support, the biomaterial being characterised in that at least one surface of the support is coated with a monoclonal antibody selected from the group consisting of monoclonal antibody A9, monoclonal antibody A18, monoclonal antibody A27, monoclonal antibody A35 and combinations thereof.

In preferred embodiments of this aspect of the present invention the monoclonal antibody is monoclonal antibody A9, monoclonal antibody A35 or monoclonal antibody A27 and most preferably monoclonal antibody A27.

In a preferred embodiment of this aspect of the present invention the support is a polymer selected from the group consisting of agarose, polyacrylamide, polyvinyl alcohol, polyester, polystyrene, polytetrafluoroethylene, expanded polytetrafluoroethylene, poly(ethylene terephthalate), polyurethane, silicon rubber and poly(-hydroxyethyl methacrylate). Preferably the polymer has free-OH groups, free amino groups, free-COOH groups or free-SH groups.

In a further preferred embodiment of the present invention the support is a ceramic, glass, metal, metal-glass, a preformed membrane, a porous material, a beaded material, a sponge or a tube.

By appropriate selection of one of the monoclonal antibodies described herein, it is possible to produce a biomaterial, the surface of which will specifically bind fibronectin or vitronectin in a manner such as to enhance or repel the attachment and growth of specific cells. As would be appreciated by a person skilled in the art, this concept of providing a biomaterial surface coated with monoclonal antibodies directed against biological molecules is applicable for molecules other than adhesive glycoproteins such as fibronectin or vitronectin. The general concept would be applicable to the use of specific monoclonal antibodies for the presentation of other biological molecules required for cell colonization of a surface, such as the presentation of growth factors that cells such as endothelial cells may require or prefer for cell growth and colonization.

As would be readily understood by a person skilled in the art, the biological factor(s) against which the monoclonal antibody is directed will depend upon the tissue in which the biocompatible material is to be implanted. For example, whilst fibronectin or vitronectin will provide attachment to most cells very little attachment between fibronectin or vitronectin and sensory nerve cells is observed. Accordingly, where the biomaterial was to be implanted and the attachment of sensory nerve cells was to be encouraged, the monoclonal antibodies would be directed against members of the family of laminins such as neurite promotion factor.

In the production of the biomaterial of the third aspect of the present invention, the monoclonal antibodies may be linked to any surface using techniques known to a person skilled in the art. This technique will obviously vary from material to material as would be readily understood, however, the general concept of the present invention enables the use of any material to which the monoclonal antibodies may be linked to produce a biomaterial.

The attachment of the monoclonal antibody to the support may be achieved by adsorption, covalent coupling, radiation grafting or adhesive bonding. In addition, the attachment of the monoclonal antibodies to the support may be achieved by use of affinity binding to a suitable affinity matrix, such as anti-mouse Ig matrix or Protein A.

In addition, as would be readily understood, the species of animal from which the monoclonal antibody is produced should be compatible to that in which the biomaterial is to be implanted, i.e. if the material is to be implanted in humans, humanized monoclonal antibodies or fragments thereof having antigen-binding activity should be used.

In a further preferred embodiment of the third aspect of the present invention more than one type of monoclonal antibody is used to coat the at least one surface of the biomaterial. For example, monoclonal antibodies directed against fibronectin and monoclonal antibodies directed against vitronectin would be used in tandem. Additionally, other monoclonal antibodies with attached growth factors which may be required or beneficial in promoting attached cells to spread and grow could be used in tandem with monoclonal antibodies against adhesive glycoproteins.

In a fourth aspect the present invention consists in a device for use in in vitro cell culture, the device having a surface adapted for contact with the cell culture, the device being characterised in that the surface adapted for contact with the cell culture is coated with monoclonal antibody A18 or A27, the monoclonal antibody being orientated such that the vitronectin binding region of the monoclonal antibody is remote from the surface.

In a preferred embodiment of this aspect of the present invention the monoclonal antibody is A27.

In a fifth aspect the present invention consists in a method of removing vitronectin from bovine plasma or serum, the method comprising the steps of:

1. providing monoclonal antibody A18 or A27 on a solid support such that the vitronectin binding region of the monoclonal antibody is remote from the solid support;
2. contacting said solid support with bovine plasma or serum containing vitronectin;
3. washing said solid support to remove the bovine plasma or serum components not bound to the solid support; and
4. recovering the washing from step 3 to obtain vitronectin-free bovine plasma or serum and/or treating the solid support to release the bound vitronectin and recovering the released vitronectin.

In a preferred embodiment of this aspect of the present invention the monoclonal antibody is monoclonal antibody A27.

At present it is preferred that the solid support is in the form of a column and the bovine serum containing vitronectin is passed through the column.

In a sixth aspect the present invention consists in a device for use in removal of vitronectin from bovine plasma or serum, the device comprising a solid support coated with monoclonal antibody A18 or A27 in a manner such that the vitronectin binding region of the monoclonal antibody is remote from the solid support.

In a preferred embodiment of this aspect of the present invention the monoclonal antibody is monoclonal antibody A27.

In a further preferred embodiment of this aspect of the present invention the solid support is in the form of a column.

In a seventh aspect the present invention consists in a method for determining the ability of a monoclonal antibody reactive with fibronectin or vitronectin to interfere with the cell binding activity of fibronectin or vitronectin comprising the following steps:

1. Contacting fibronectin or vitronectin with a solid support coated with the monoclonal antibody to be tested;
2. contacting the solid support from step 1 with the monoclonal antibody to be tested;
3. contacting the solid support from step 2 with a biological material reactive with the cell binding region of fibronectin or vitronectin; and
4. measuring the amount of the biological material bound to the solid support.

In a preferred embodiment of these aspects of the present invention the biological material reactive with the cell binding region of fibronectin or vitronectin is cells.

In an eighth aspect the present invention consists in a method for assaying the adhesive activity of fibronectin or vitronectin or fragments thereof in a sample comprising the following steps:

1. Contacting a solid support with the sample, the solid support being coated with a monoclonal antibody or group of monoclonal antibodies-directed against fibronectin or vitronectin, the monoclonal antibody being reactive with an antigenic site on the fibronectin or vitronectin molecule remote from the cell binding region;
2. contacting the solid support from step 1 with either
   (a) a biological material reactive with the cell binding region of fibronectin or vitronectin; or
   (b) a labelled monoclonal antibody directed against fibronectin or vitronectin, the monoclonal antibody being reactive with the fibronectin or vitronectin molecule at a site at or adjacent the cell binding region; and
3. measuring the amount of bound labelled monoclonal antibody or the amount of bound biological material.

In a preferred embodiment of this aspect of the present invention the monoclonal antibody on the solid support is selected from the group consisting of monoclonal antibody A9, monoclonal antibody A27 and monoclonal antibody A35.

In a further preferred embodiment of this aspect of the present invention the labelled monoclonal antibody is selected from the group consisting of monoclonal antibody A7, A14, A17, A18, A24 and A32.

It is also preferred that the biological material reactive with the cell binding region of fibronectin or vitronectin is cells.

By using monoclonal antibodies, the activities of which are known, a bioassay of the adhesive activity of fibronectin or vitronectin is provided which is more sensitive and has a more persistent end-point than the standard format of such assays. The use of solid phase domain specific monoclonal antibodies provide a means for a sensitive specific assay for the functional state of particular antigens in a manner similar to that presently described for cell adhesion, in parallel with quantitative assays.

The method as used in the present invention of adsorbing adhesive glycoproteins to a surface with specificity and affinity, and of precisely controlling the orientation of glycoprotein, has application in the immunoassay of the biological activity of glycoproteins and of complex biological samples which contain such glycoproteins. One immediate application of the specific monoclonal antibodies described in the invention is for the purification of vitronectin from bovine plasma or serum, for use in research or in vitro cell culture etc. A particular use of purified vitronectin or of serum depleted of vitronectin is in the study of cellular adhesion reactions, as exemplified in the Example 3 of the invention, which describes the importance of serum vitronectin in cellular attachment to polymeric plastic surfaces during cell culture in vitro. A further application of such immobilized monoclonal antibodies is in improved bioassays of the content of specific adhesive glycoproteins or fragments thereof in complex biological samples, particularly those of clinical relevance.

It is believed that the method of the eighth aspect of the present invention may have particular relevance in a number of clinical situations. This method will provide an accurate assessment of adhesive activity of fibronectin or vitronectin in a sample and will enable the analysis of crude specimens. This method may be applicable for diagnosis in any disease state in which it is anticipated that a change in the circulating plasma levels of intact fibronectin or fragments thereof, or the biological activity of the circulating plasma fibronectin is modified from normal levels, or where it is anticipated that failure of the organs that contribute to the circulating plasma pool of fibronectin could occur. Such examples are cancer, particularly where metastatic rumour spread occurs, but also diabetes and failure of the liver or kidneys.

In general, the method will be conducted on a sample in which the amount of fibronectin or vitronectin present is known. The adhesive activity of fibronectin or vitronectin in the sample would then be compared against a standard.

Another advantage offered by this method is that when labelled monoclonal antibodies are used in Step 2 this does away with the necessity of cell culture.

The observations in Example 3 for the role of adhesive glycoproteins in cellular attachment to polymeric plastics are of direct relevance to the design of biomaterials, and point to another application of the invention. That application is to improve that biological compatibility of biomaterial surfaces or to enhance cell colonization of biomaterial surfaces. For this purpose, the invention describes the use of monoclonal antibodies, either those described in the Examples of this invention or others, in immmobilized form on the surface, so that the antibody will bind adhesive glycoproteins in a specific manner and with high affinity, so presenting on the surface a biological signal that will be recognized by other biological molecules and/or enhance or repel the attachment and growth of specific cells. The ability by this method to control the nature of cellular attachment to the surface of a biomaterial will overcome or alleviate some of the disadvantages of the existing art.

The design of the biomaterial surface would be advantaged if the adsorption of the glycoprotein could be bound specifically and held with high affinity by the biomaterial surface and this is possible by using monoclonal antibodies as the binding site. The design of the present invention has the additional advantage that the adsorbed glycoproteins could be derived from the plasma or serum of the patient, and the plasma or serum could be used without requirement to purify the adhesive glycoprotein from the plasma or serum.

In order that the nature of the present invention may be more clearly understood preferred forms thereof will now be described with reference to the accompanying drawings and following examples.

DESCRIPTION OF THE FIGURES

FIG. 1

Stained Gel and Western Blot of Affinity Purified Vitronectin Antigen 12 ug antigen run on 9% acrylamide under reducing conditions.

Positions of molecular wt. standards are indicated in kilo daltons.

A. Gel stained with Coomassie brilliant blue.
B. Western blot of gel probed with A27.

FIG. 2

Western Blot of Vitronectin Antigen Probed With Monoclonal and Polyclonal Antibodies Samples are: tracks 1 and 5, extracellular matrix (ECM) from bovine corneal endothelial cells tracks 2 and 6 2 ul FCS tracks 3 and 7 2 ul FCS after passage over an A27-AFFIGEL 10 column tracks 4 and 8 1 ug affinity purified antigen.

Tracks 1–4 were probed with rabbit anti-bovine vitronectin antiserum diluted 1/100 in blocking buffer.

Tracks 5–8 were probed with A27 (1/500 dilution of ascites fluid in blocking buffer).

FIG. 3

Binding of Anti-Vitronectin Antibodies to Vitronectin

Titration of purified Mab A27 (□) and Mab A18 (Δ) on purified bovine vitronectin antigen coated at 250 ng/ml.

FIG. 4

Affinity Purification of Antigen on A27-Affigel 10

Absorbance at 280 nm.

Antigen detected by A27 or A18. Fraction samples were diluted 1/50 in PBS and used to coat duplicate wells of an ELISA plate. The ELISA was done as described in Materials and Methods.

FIG. 5

Western Blot of Purified Antigen Separated by SDS PAGE on 9% Acrylamide and Probed With A27

Track 1. 750 ng antigen run under non-reducing conditions.

Track 3. 750 ng antigen run under reducing conditions.

Track 4. 750 ng antigen incubated for 1 hr at 37° C. with 9 units of thrombin (Sigma) prior to electrophoresis under reducing conditions.

Track 5. 750 ng antigen pre-incubated for 24 hr at 37° C. with 9 units of thrombin.

Molecular wts of standards are indicated in kilo daltons.

FIG. 6

Binding of Antigen to Heparin Sepharose

Absorbance at 280 nm.

Figure 4:
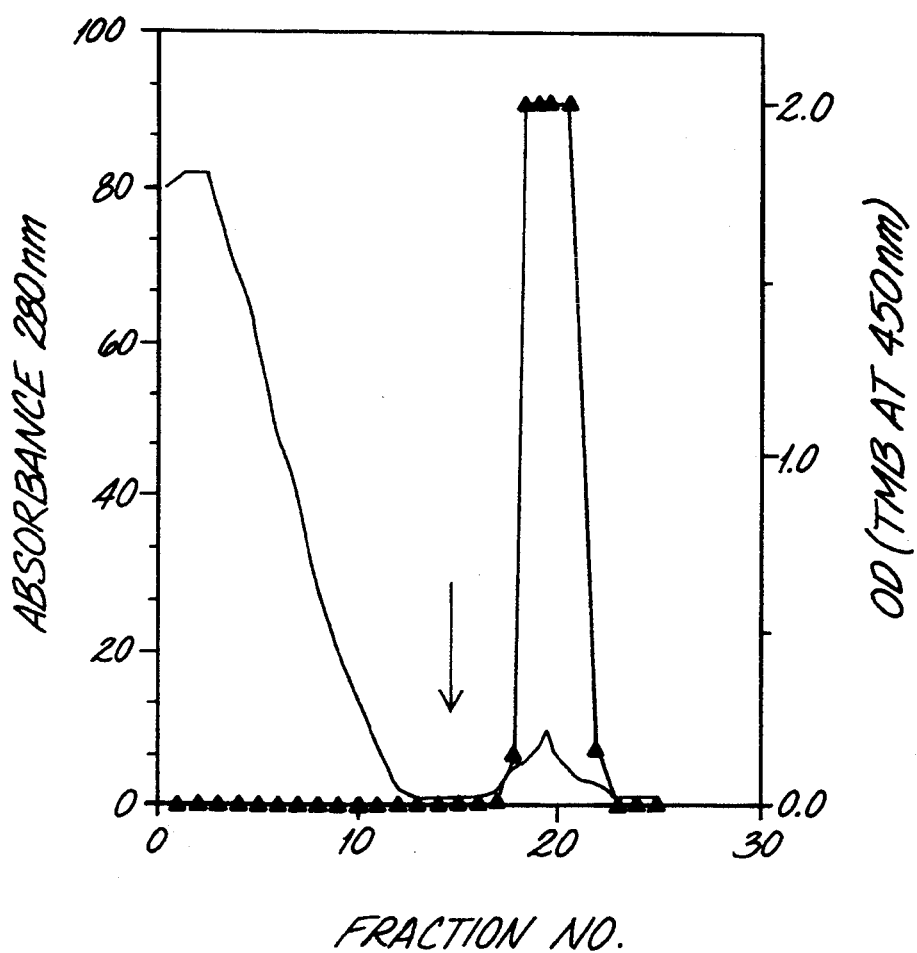

Fractions titrated for antigens as in FIG. 4.

Absorbance at 450 nm (OPD).

Profile of detection of native antigen with A27.

Profile of detection of denatured antigen with A27.

Arrow denotes start of high salt buffer (0.5M NaCl, 0.05M Tris/Cl pH 7.5).

FIG. 7

Vitronectin Content of Fetal Calf Serum (FCS) and of the Same FCS After Passage Over an Affinity Column Consisting of Immobilized Anti-Vitronectin Antibody

FIG. 8

Titration Curve of Purified Vitronectin (□—□) and Raw Serum (■—■)

FIG. 9

Cross Reactivity of Anti-bovine Fibronectin Antibodies With Human Fibronectin

FIG. 10

Cross Reactivity of Anti-bovine Fibronectin Antibodies With Human Fibronectin Fragments

FIG. 11

Cross Reactivity of Anti-Bovine Fibronectin Antibodies With Human Fibronectin Fragments

FIG. 12

Comparison of Cell Adhesion to Fibronectin/Vitronectin Coated on Antibody or Plastic Conditions were as described for the assay 1 (see Materials & Methods, Example 3).

Adhesion at 1 hr.

Abscissa: coating concentration of fibronectin (●○) or vitronectin (▲Δ) on antibody (—) or plastic (  ). Antibodies were A22 (●) and A27 (▲).

FIG. 13

Adhesion of BHK-21 Cells to Fibronectin Specifically Absorbed From Human Plasma By A35 In Comparison to A22 and A27

FIG. 14

Titration of Fibronectin Binding to A35 From Raw Plasma By Elisa Using Biotinylated Monoclonal Antibodies A9 (—●—), A14 (—■—) and A32 (—▲—)

EXAMPLE 1

Preparation and Characterisation of Monoclonal Antibodies Against Vitronectin and Fibronectin Materials and Methods.
Monoclonal Antibodies to Bovine Vitronectin and Fibronectin.

The extracellular matrix of cells in culture is rich in both fibronectin (FN) and vitronectin (VN) (Gospodarowicz et al. 1980); Neyfakh et al. 1983; Baetscher et al. 1986). Extracellular matrix material (ECM) from bovine endothelial cells was used to provide immunogenic fibronectin and vitronectin in their native form. Cell-free ECM was prepared by 2×5 min incubations of culture dishes of endothelial cells in 0.02N NaOH (Gospodarowicz & Lui, 1981). The ECM was rinsed with PBS and scraped into 0.5–1.0 ml Dulbecco's phosphate buffered saline A(PBS), per $10^7$ cells. Female BALB/c mice were immunized interperitoneally with ECM from $10^7$ cells per mouse. After 3–6 months animals received similar booster injections. Those producing antibody reactive in enzyme-linked immunoassay (ELISAs) with ECM (prepared from endothelial cells grown in 96 well tissue culture plates), were rested for 6 weeks, given a further boost and used for cell fusion 3 days later. Spleen cells were fused with Sp2/0 myeloma cells, and hybrid cultures were grown as previously described (Underwood, 1982). Supernatants from confluent wells were screened against ECM by ELISA as previously described (Underwood, 1985) with the following modifications. Incubations were done in 50 ul per well. All washes were reduced from 5 min to 3 min. After incubation with peroxidase conjugated rabbit antimouse immunoglobulins (RAM, Dako) plates were washed four times with PBS before addition of 100 ul per well O-phenylene dismine substrate (OPD, Sigma). Colour development was terminated after 3-30 min by addition of 25 ul per well of 0.4% sodium azide using a dropper. Absorbances were read on a Dynatech MR600 plate reader at 450 nm (ref. 630 nm). Positive hybridomas were further screened for activities against FN and VN by ELISA and Western blotting against bovine FN (Sigma) or dilutions of serum. Hybridomas were cloned by microscopic picking of single cells (Underwood & Bean, 1988). Antibody subclasses were determined by immunodouble diffusion against subclass specific antisera (Litton Bionetics) or by ELISA on ECM using subclass specific peroxidase-conjugated second antibodies (Litton Bionetics). Large quantities of antibody were prepared by growing hybridomas as ascites in BALB/c mice primed 7-14 days earlier with 0.5 ml pristane (Aldrich). Antibody was purified from ascites fluid by affinity chromatography on protein A SEPHAROSE (Pharmacia Fine Chemicals, an agarose bead support medium) as previously described (Underwood et al. 1983). Non-specific mouse antibody of various subclasses was prepared by fractionation of normal mouse serum on protein A Sepharose or from pools of anti-influenza monoclonal antibodies. Polyclonal antibodies to FN and VN were prepared in New Zealand white rabbits. The immunoglobin fractions of sera were prepared in New Zealand white rabbits. The immunoglobin fractions of sera were prepared by chromatography on protein A Sepharose. In addition, rabbit anti-bovine vitronectin antiserum was a generous gift from E. Ruoslahti.

Additive Binding and Antibody Blocking Assays.

The degree of additive binding of monoclonal antibodies (MAbs) was determined by solid phase RIA (essentially as in Steele, J. G. et al., 1985). Antibodies A18 and A27 were iodinated with $^{125}$I by the chloramine T method (Stahi, C., et al., 1983). The assay was performed by incubating 250 ng/ml of each $I^{125}$-labelled monoclonal antibody or of a $I^{125}$-labelled IgG control antibody for 2 hr at room temperature, then determining the amount of $I^{125}$ bound after washing the plate with 4 washes.

Electrophoresis and Western Blotting.

The sodium-dodecyl sulphate polyacrylamide gel (SDS-PAGE) system of Laemmli (1970) was used with the addition of 0.5M urea throughout. Samples were prepared as follows. 10 cm dishes of bovine corneal endothelial cells were split 1:2 and maintained untouched for 7 days. The monolayers were washed with serum-free medium 199 (SF199) and incubated with 10 ml SF199 for 1 hr at 37° C. This was replaced with fresh SF199 and the plates were incubated for 24 hr. The conditioned medium was removed and concentrated 10 fold by dialysis against crystalline sucrose. (The dialysis tubing was pre-blocked by incubation in 1% bovine serum albumin (BSA) in water for 1 hr at room temperature and then thoroughly rinsed with water.) Aliquots of the concentrated condition medium were stored at −20° C. and mixed 1:1 with SDS sample buffer for electrophoresis. The cell layer was harvested by 2×5 min incubations with 0.5 ml of 0.02N NH₄OH. This material was stored at −20° C. and used as described for conditioned medium. Following a rinse with 0.02N NH₄OH and two washes with PBS, ECM was extracted by overnight incubation on an orbital shaker at 37° C. with 1.0 ml 1% SDS In 0.1M Tris/Cl pH 7.6. This was followed by 30 min at 50° C. Matrix material was scraped off the dish and mixed 1:1 with SDS sample buffer. Aliquots were stored frozen at −20° C. Samples were heated in boiling water for 3 min prior to gel application. Acrylamide concentration in the resolving gel ranged from 7.5-10%, and gels were run at 40 volts overnight in a Biorad Protean 16 cm electrophoresis apparatus. Protein bands were transferred to nitro-cellulose sheets (BM85, Schleicher and Schuell) by the method of Erickson et al. (1982). Transfer was carried out for 3 hr at 7 volts per cm in a Hoeffer transfer apparatus. Following transfer the membranes were washed and blocked overnight at 4° C. with 3% bovine serum albumin (BSA) in Tris buffered saline. 15M NaCl, 0.05M Tris-chloride pH 7.5 (TBS). Immunological activity was detected by 1.5-2 hr incubation with MAb or rabbit antiserum followed by 4×5 min washes in TBS, peroxidase was detected using 4-chloro-1-napthol (Hawkes, R., et al, 1982) in 0.05M Tris chloride pH 7.6.

Results

Monoclonal Antibodies

Figure 1:
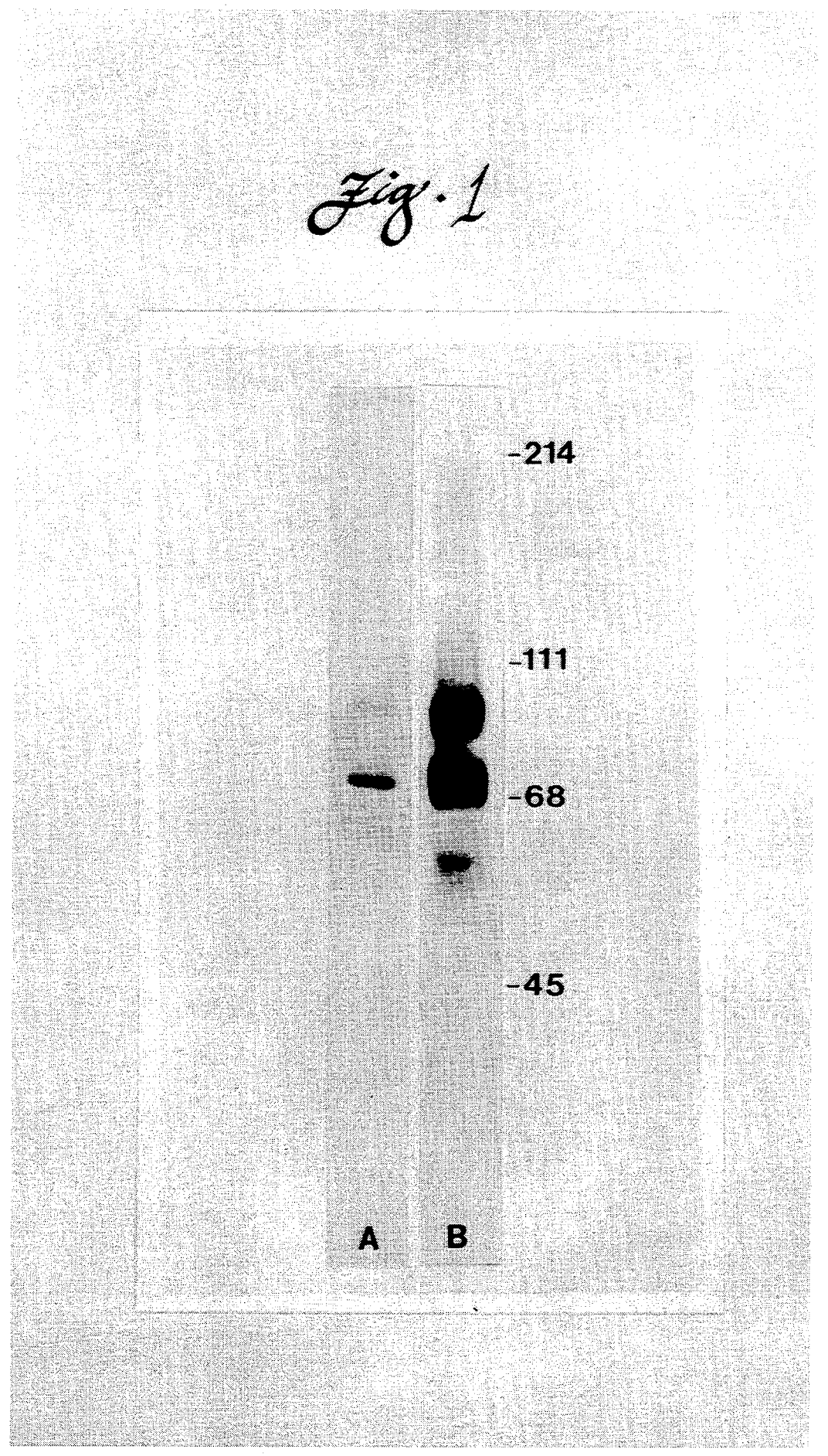
Figure 2:
Figure 3:
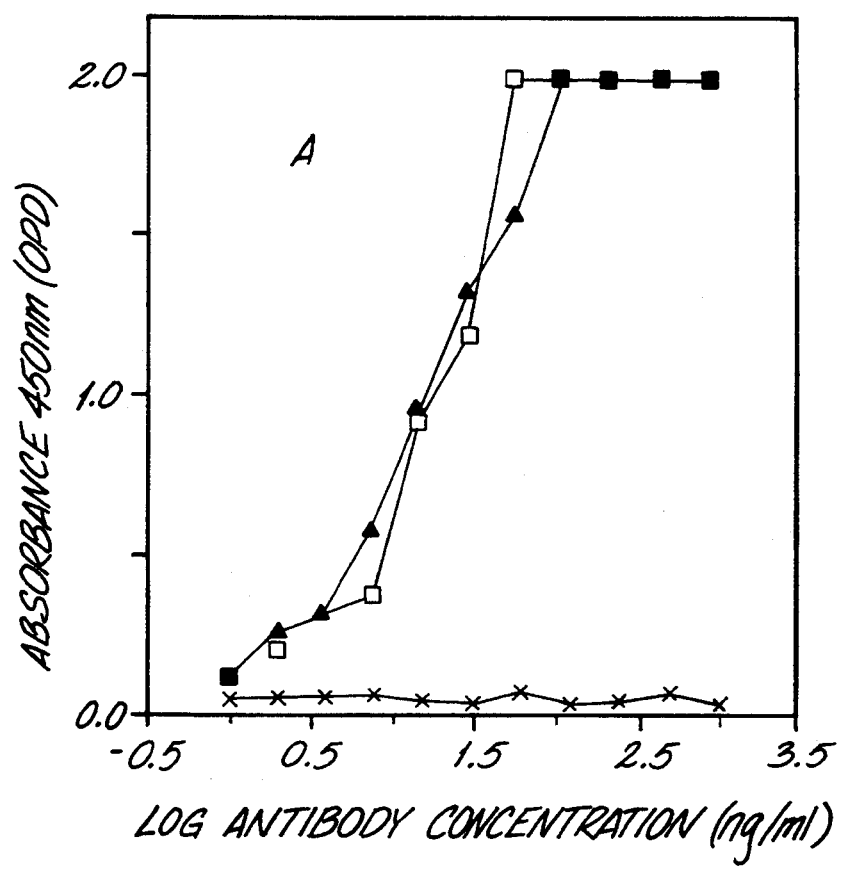

Twenty hybridomas showing specificity for FN in ELISAs were successfully cloned and grown as ascites. Two additional hybridomas displayed activity towards bovine serum in ELISAs with serum coated at high dilutions (1/5000). The characteristics of the twenty two antibodies are shown in Table 1. The molecular weights of serum components reactive with MAb A27 in western blots agreed well with those reported for bovine VN (Hayman et al. 1985b). An affinity column of MAb A27 (see Example 2 for methods and affinity chromatography results) was used to prepare antigen from fresh bovine plasma or serum. A protein stain and western blot of affinity purified antigen are shown in FIG. 1. No bands were detected by protein staining which were not detected by A27, indicating a high degree of purity of the antigen (see Example 2 for further details). Its identity with bovine VN was demonstrated by probing a "western blot" with rabbit antiserum to bovine vitronectin (kindly donated by E. Ruoslahti). As shown in FIG. 2 this antiserum was reactive with purified antigen (track 4) and showed a similar profile of reactivity with ECM (track 1) and foetal calf serum (FCS) (track 2) to MAb A27 (tracks 5,6,8). MAb A18 was not reactive in western blots but displayed similar levels of activity towards purified antigen in ELISAs as MAb A27 (FIG. 3). The two antibodies displayed additive binding when added simultaneously in ELISAs. The results of an additive binding experiment are shown in Table 2. (Results of a second experiment were essentially similar to those shown in Table 2). Additive binding (greater than 85%) was observed, indicating that the two antibody binding sites were separate enough as for there to be no steric hindrance to occur between A18 and A27. The two monoclonal antibodies were binding to the

TABLE 1

Characteristics of Monoclonal Antibodies

| Antibody | Heavy chain subclass | Reactivity on[1] western blots | Reactivity with FN in ELISA | Reactivity with dilutions of FCS[2] |
|---|---|---|---|---|
| A2 | G1 | 220(doublet) | + | 0.15 |
| A3 | G1 | — | + | ND |
| A4 | G1 | 220 | + | 0.4 |
| A5 | G1 | — | + | ND |
| A7 | G1 | — | + | ND |
| A9 | G2a | 220(doublet) | + | 0.15 |
| A10 | G1 | — | + | ND |
| A12 | G1 | 220(faint 180) | + | 0.7 |
| A14 | G1 | 220(faint 180) | + | 0.5 |
| A17 | G1 | 220 | + | 0.7 |
| A19 | G1 | 220 | + | 0.7 |
| A20 | G1 | 220 | + | 0.8 |
| A22 | G1 | 220 | + | 0.6 |
| A23 | G1 | 220 | + | 0.8 |
| A24 | G2b | — | + | 1.0 |
| A25 | G2a | 220 | + | >2 |
| A26 | G1 | 220 | + | 0.2 |
| A28 | G1 | 220 | + | >2 |
| A32 | G1 | 220 | + | 0.6 |
| A35 | G1 | 220 | + | 0.6 |
| A18 | G1 | — | — | 1.7 |
| A27 | G1 | 83,72(60) | — | >2 |

[1]Approximate molecular weights of reactive bands in kilodaltons.
[2]ELISA, maximum absorbance at 450 nm.

TABLE 2

Additive binding of antibodies A18 and A27

| Antibody | cpm bound/well | theoretical additivity | observed additivity |
|---|---|---|---|
| (a) Tray precoated with 0.5 ug/ml purified vitronectin | | | |
| IgG control | 405* | — | |
| A18 | 2,106 | — | |
| A27 | 3,692 | — | |
| A18 + A27 | 5,790 | 5,798 | 99.7% |
| (b) Tray precoated with 5 ug/ml purified vitronectin | | | |
| IgG control | 532* | — | |
| A18 | 25,830 | — | |
| A27 | 19,119 | — | |
| A18 + A27 | 41,974 | 44,949 | 86.8% |

*Subtracted from other wells precoated with the same concentration of vitronectin, as "non specific" binding same antigen, as shown in another experimental format. When unlabelled A18 was coated onto a tray and then vitronectin immobilised by attachment to that A18, $I^{125}$-labelled A27 could then bind extensively to the vitronectin (12,873 cpm bound/well) whereas $I^{125}$-labelled A18 could not (only 1251 cpm bound/well). Conversely, when unlabelled A27 was coated onto a tray and then vitronectin immobilised by attachment to that A27, subsequent incubation with $^{125}$I-A18 gave extensive binding (22,640 cpm bound/well) whereas with $^{125}$I-A27, there was little binding (2754 cpm bound/well). These results argue against any possibility that A18 binds to a different protein to A27, but indicate that A18 and A27 recognise epitopes that are quite distant from one another. It should be noted that vitronectin bound to immobilised A27 presents a surface that is conducive to cell attachment, whereas vitronectin bound to immobilised A18 is inactive for cell attachment (see Example 3). This binding data also shows, therefore, that A18 may be used as an immunological probe for determining whether vitronectin adsorbed onto a surface is held in a conformation which presents the cell binding regions in an accessible and therefore active configuration. The anti-fibronectin monoclonal antibodies displayed a variety of binding profiles to pure Fn coated on ELISA plates, indicating a wide range of antibody affinities.

EXAMPLE 2

Use of Immobilized Anti-vitronectin Antibodies in Affinity Chromatography to (a) Rapidly and Effectively Purify Vitronectin in a Single-Step Procedure and Quantitatively Deplete Bovine Serum or Plasma of Vitronectin Materials and Methods.
Monoclonal Antibody Affinity Columns Purified antibodies were dialysed against 0.1M Hepes buffer pH 7.5 and adjusted to 2 mg/ml using BSA as standard (Lowry et al. 1951). Antibody was conjugated to AFFIGEL 10 (BioRad Laboratories Inc., a polyacrylamide or agarose bead support medium which is chemically activated to covalently bind molecules such as antibodies at the rate of 1 ml antibody per 2 ml packed gel by the method of Mayes (1984). The conjugate was packed into the body of a syringe. VN was prepared from bovine plasma or serum by this method, using monoclonal antibody A27. Solutions containing antigen were applied to the column at 0.1 ml/min, washed with several volumes of high salt buffer (0.5M NaCl, 0.05M Tris chloride pH 7.5) and eluted with 3M $MgCl_2$, 0.1M Tris pH 7.0. After elution, columns were washed alternately with high salt buffered with 0.1M Tris at pH 8.5 and with 0.1M acetate at pH 4.0, and stored in PBS at 4° C. with 0.08% sodium azide as preservative. Antigen was detected in eluted fractions by ELISA on plates coated with dilutions of fraction samples. Fractions containing antigen were pooled, dialysed against TBS and their protein content estimated by the method of Sorenson & Brodbeck (1987).

Yield of Purified Vitronectin Using the A27 Affinity Column Method

Purified vitronectin was assayed for protein content using the Biorad BCA reagent and bovine serum albumin as standard.

Dilutions of raw bovine serum, and vitronectin purified from the same serum batch were coated in parallel on Dynatech flexible ELISA plates, for 2 days at 4° C. in quadruplicate. (At dilutions of >1/100 the coating of vitronectin from serum is quantitative—see Underwood and Bennett 1989).

Vitronectin coated to the wells was detected by ELISA using purified monoclonal antibody A27 at 1 ug/ml, corrected for non-specific binding of 1 ug/ml of purified mouse IgG1. Titration curves were drawn from the absorbance values and concentration of vitronectin in raw serum calculated from the displacements of the curve.

Results

Figure 8:
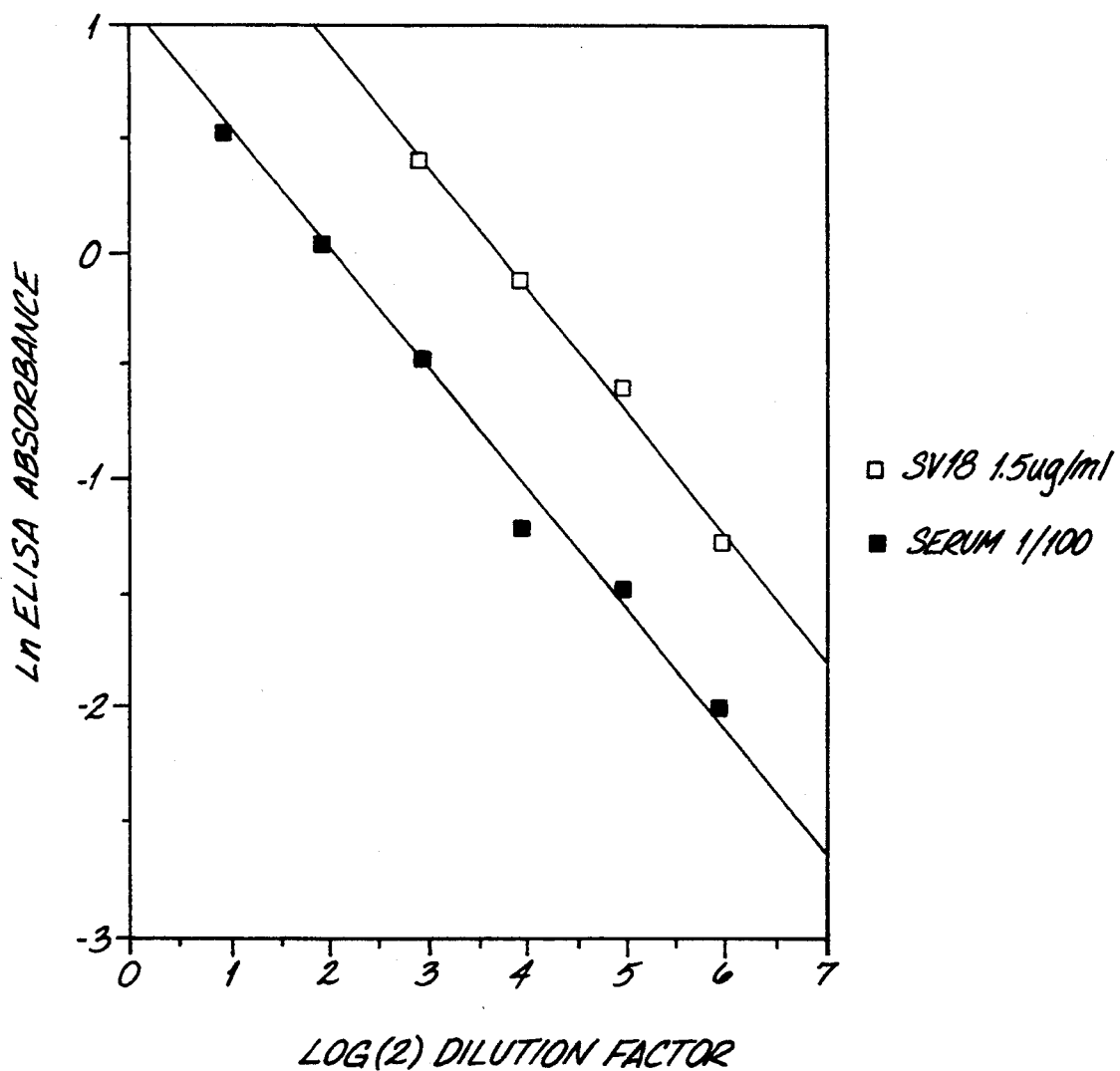

The concentration of vitronectin purified from a 40 ml sample of bovine serum was found to be 355 ug/ml. The total volume of purified material was 6.0 ml, and the total yield was 2.13 mg. In terms of the original 40 ml serum sample, this represents a yield of 53.25 ug/ml. The horizontal displacement in the titration curves in FIG. 8 was 1.5 $\log_2$. The starting concentration of the purified vitronectin in the assay was 1.55 ug/ml, and the starting dilution of the raw serum was 1/100. Therefore the concentration of vitronectin in the raw serum can be calculated as $1.55 \div 2^{1.5} \times 100 = 55$ ug/ml. Therefore the percentage yield of purified vitronectin from the raw serum $= 53.25 \div 55 \times 100 = 96.8\%$.

Cell Adhesion Assays.

Dilutions of adhesive molecules in PBS were coated onto 35 mm plastic bacteriological dishes (Bunzl, Australia) by incubation for 1 hr in a humidified 37° C. incubator. The coating solution was removed and replaced with blocking buffer (1% BSA in PBS). After a further 1 hr incubation at 37° C. the plates were rinsed 3 times with serum free Iscove's medium (SFI) (Gibco). BPLK-21 fibroblast cells were disaggregated from monolayers with minimal exposure to 0.05% trypsin/0.02% EDTA (trypsin/EDTA). This was neutralized by the addition of 10 volumes of SFI containing 0.02% soy bean trypsin inhibitor (Sigma). The cells were centrifuged and resuspended in SFI+1% BSA. Between $3 \times 10^5$ and $10^6$ cells in 1 ml SFI plus BSA were added to each dish. After incubation for 30 min to 1 hr at 37° C. in a humidified incubator the medium in each dish was pipetted gently to suspend non-adherent cells and samples were removed for counting in a haemacytometer.

Techniques for electrophoresis and for ELISA assays: see Example 1.

Results

Use of Immobilized Anti-Vitronectin Antibodies in Affinity Chromatography to Purify Bovine Vitronectin.

The elution profile of 2 ml of FCS on A27-Affigel 10 is shown in FIG. 4. A similar profile was obtained with plasma. It can be seen that during this single step procedure, a single peak of vitronectin antigen was eluted with 3M $MgCl_2$ (fractions 18-22 in FIG. 4). This material was dialysed against three changes of TBS over 24 hr and stored at 4° C. with 0.08% azide in silicon coated tubes.

Characterization of the Purified Vitronectin:

1. Electrophoresis and Western Blotting.

Figure 5:
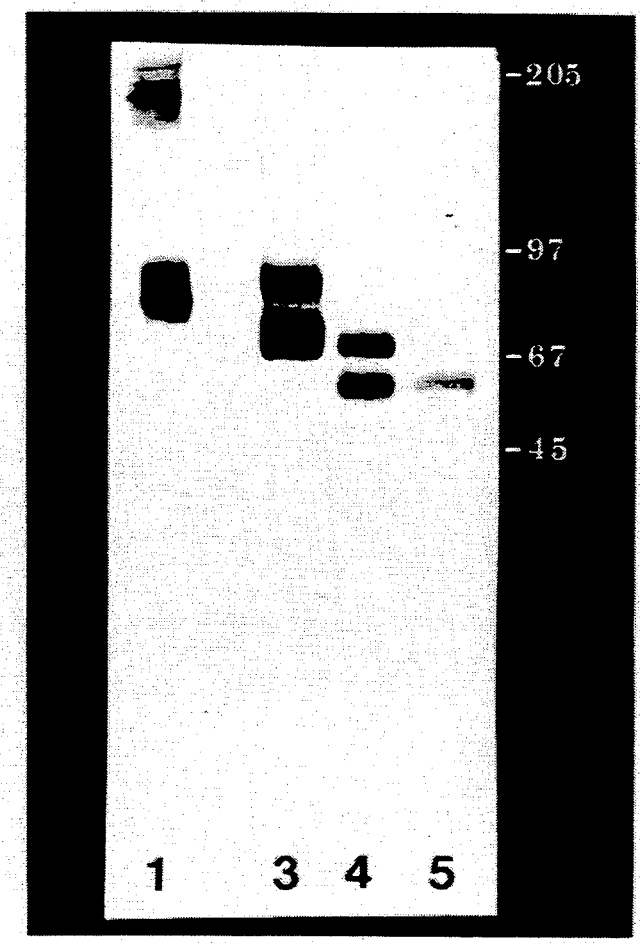

To test for purity of antigen, 12 ug of affinity purified material were run per slot on a 9% acrylamide SDS gel under reducing conditions. The protein-stained gel and corresponding western blot probed with A27 are shown in FIG. 1. The protein stain revealed two bands of approximate molecular wts. of 83 and 72 KD respectively (FIG. 1A). Both bands were detected on the western blot with A27, and at this protein loading were considerably over-developed, giving diffuse staining (FIG. 1B). A third band was detected on the blot of molecular wt. 60 KD, and two minor bands were detectable around 180 KD. No bands were detected by protein staining which were not detected by A27, indicating a high degree of purity of the antigen. Purified antigen was run on a second gel either with or without reduction, and following thrombin treatments of 1 or 24 hr duration, to compare the behaviour of bovine vitronectin with that reported for the human molecule. The results are shown in FIG. 5. when run under non-reducing conditions a single major band of approximately 80 KD was observed with a smaller band at 180 KD (track 1). Reduction of the antigen produced the 72 KD and 83 KD bands seen before (track 3). These molecular weights agree well with those for human and bovine vitronectin reported by others (Hayman et al, 1983; Barnes, D. W., et al, 1983; Hayman, E. G., et al, 1985a; Akama, T., et al, 1986; Dahlback, B., and Podack, E. R., 1985; Preissner, K. T., et al. Upon storage of the antigen the relative amount of the 83 KD component decreased and tat of the 72 KD component increased. Thrombin treatment resulted in a relatively rapid breakdown of the larger component and slower breakdown of the smaller components to produce a major product at 60 KD (FIG. 5, tracks 4 and 5). Treatment of human vitronectin with thrombin prior to SDS electrophoresis with reduction, has been reported to produce a major fragment of molecular wt. 57-60 KD (Silnutzer, J and Barnes, D. W. 1984; Tomasini, B. R. and Mosher, D. F., 1986. Our results are very similar to those of the latter authors with relatively rapid disappearance of the high molecular wt. band and slower disappearance of the smaller component.

2. Binding to Antithrombin III.

Binding of human vitronectin to antithrombin III coated on plastic has been described (IU, C. R., and Ruoslahti, E., 1985). The ability of the bovine antigen to attach to antithrombin III coated on plastic was tested as follows. After coating with antithrombin III and blocking with BSA, 50 ul of antigen per well were added at 200 ng/ml in blocking buffer. This was incubated at room temperature for 2 hr followed by $3 \times 3$ min washes in blocking buffer. The ELISA was then continued as described in Materials and Methods for Example 1. Controls contained (a) no antithrombin III, (b) no antigen, and (c) non-specific IgG1. The results are shown in Table 3. It is clear that at coating concentrations at and above 10 ug/ml of antithrombin III, both antibodies A27 and A18 were specifically bound in the presence of antigen but not in its absence. This not only indicates that the antigen binds to antithrombin III but that the

TABLE 3

| Binding of Antigen to Antithrombin III | | | |
|---|---|---|---|
| | Antithrombin III coating concentration ug/ml | | |
| Antibody | 1 | 10 | 100 |
| (a) DIRECT BINDING OF ANTIBODY TO ANTITHROMBIN III COATED PLATES | | | |
| IgG1[a] | 0.00[b] | 0.00 | ND |
| A27 | 0.06 | 0.08 | ND |
| A18 | 0.01 | 0.01 | ND |
| (b) BINDING OF ANTIBODY TO ANTITHROMBIN III COATED PLATES TREATED WITH ANTIGEN[c] | | | |
| IgG1 | 0.00 | 0.01 | 0.04 |
| A27 | 0.05 | 0.65 | 0.70 |
| A18 | 0.05 | 0.35 | 0.43 |

[a] Control IgG1 purified from normal BALB/c mouse serum
[b] Optical density of OPD at 450 nm, corrected for coating with buffer only. Means of duplicates. ND = not done.
[c] After blocking the coated plate with BSA, antigen was added at 200 ng/ml and reacted for 2 hr, after which time unbound antigen was washed off and purified antibodies added at 1 ug/ml.

binding site is not in the vicinity of either of the antibody binding sites.

3. Binding to Heparin.

Figure 6:
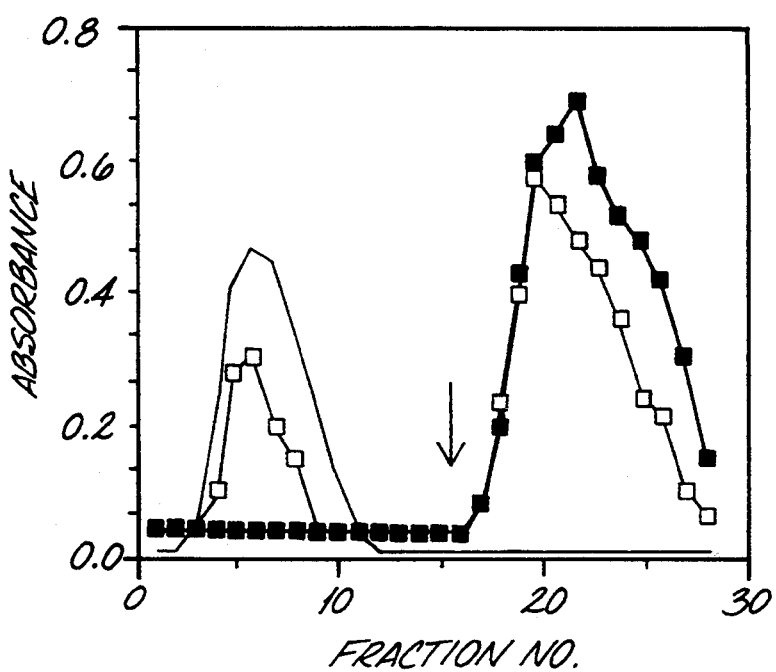

The binding of human vitronectin to heparin has been described (Hayashi, M., et al., 1985; Barnes, D. W. et al, 1985, and these authors reported increased binding of vitronectin denatured by heat, urea or guanidine hydrochloride. The binding of the bovine antigen to heparin was tested by affinity chromatography on heparin-Sepharose (Pharmacia). A one ml column was preincubated with ELISA blocking buffer to saturate non-specific binding sites. Approximately 20 ug of antigen in 0.5 ml TBS was either held in boiling water for 5 min prior to loading, or applied directly to the column, at a flow rate of 0.1 ml/min. The column was washed with 3 volumes of TBS and eluted with high salt buffer, collecting 200 ul fractions. (Since the amount of protein loaded was below the detection limit of the UV monitor attached to the column, a small amount of phenol red was added to the sample to mark the elution of non-bound material). 50 ul samples of fractions diluted 1/50 in PBS were coated on ELISA plates overnight at 4° C., then antigen was detected with ELISA using A27 at 50 ng/ml. The results are shown in FIG. 6. A small proportion of native antigen failed to bind to the heparin column, while all of the denatured antigen was bound. Bound antigen eluted in the high salt buffer.

4. Cell Adhesion.

Both human and bovine vitronectin have been reported to promote cell adhesion (Hayman, E. G., et al, 1985a; Hayman E. G., 1985b; Silnutzer, J. E., et al, 1985). The results of the cell adhesion studies are shown in Table 4. Clearly the vitronectin antigen promoted the adhesion of BHK-21 cells to surfaces which were refractory in the absence of antigen. Most cells adhered within

TABLE 4

Cell adhesion to vitronectin antigen and inhibition by antibody and RGDS

| Treatment | Count of non-adherent cells[a] | % adhesion[b] |
|---|---|---|
| No antigen | 28.75 | 0 |
| 0 ug/ml RGDS[c] | 6.0 | 79.1 |
| 200 ug/ml RGDS | 11.25 | 60.9 |
| 400 ug/ml RGDS | 22.25 | 22.6* |
| 600 ug/ml RGDS | 23.0 | 20.0* |
| 800 ug/ml RGDS | 25.0 | 13.0* |

[a]Mean of four to nine replicates
[b]% adhesion given by 100 × (C − non-adherent cell count)/C where C = non-adherent cell count in the absence of antigen or fibronectin.
[c]Antigen coated at - 4 ug/ml. Specified concentrations of RGDS added with cells.
*Significant inhibition of adhesion (p < 0.01). (Analysis of variance and Student Newman Keuls tests.)

30 min and were spread and flattened by 1-2 hr.

Comparison to Previous Method for Purification of Vitronectin.

Human vitronectin has been purified by affinity chromatography using an immobilized monoclonal antibody (Hayman, E. G. et al, 1983) however this method has not been previously available for the purification of the bovine molecule, as the monoclonal antibody used by previous workers does not bind to bovine vitronectin.

The previous method of purifying bovine vitronectin was based upon the finding that vitronectin binds to certain glass beads, and involved preliminary steps of removing the serum albumin by chromatography on an AFFIGEL Blue column, then chromatography on a protein A-SEPHAROSE column in order to remove IgG from the serum. This subsequent chromatography on glass beads involves a pH-dependent elution sequence, and gives a preparation of vitronectin which is active for cell attachment, but is not adequately pure for biochemical or immunological studies. Further purification by ion exchange chromatography or by other (non-immunological) affinity chromatography techniques have been necessary to remove impurities from the vitronectin as prepared by the glass bead chromatography technique. As a consequence, the previous techniques for the purification of bovine vitronectin are much more lengthy procedures than the single affinity column procedure described in this Example.

Hayashi, M. and Kraus, W (EP0292663 "Isolating vitronectin from biological materials") describes a method of purifying vitronectin which may be applied to bovine plasma or serum. This method involves treatment of the sample with 4–8M urea in order to partially denature the vitronectin, thereby enabling affinity adsorption to immobilised glycosaminoglycans to be used to recover vitronectin in a single step procedure. The recovery was described as being 10–40%.

The method of purifying bovine vitronectin and of removing vitronectin from bovine plasma or serum described in the present application has advantages over this prior art. The use of A27 enables vitronectin to be selectively removed from bovine plasma or serum in a single Step procedure which is quantitative (no detectable vitronectin in sample following contact with the A27-matrix, as determined by ELISA). Furthermore, the present procedure does not require exposure of the entire biological material to denaturing agents, as does the Hayashi procedure, and so serum or plasma depleted of vitronectin by the A27 column may be used immediatley either for purification of other and denaturation-sensitive factors or proteins, or for a tissue culture medium component. A27 gives a novel affinity matrix which has an interaction with bovine vitronectin which has a sufficiently high affinity as to quantitatively remove vitronectin from the biological preparation, but has a sufficiently low affinity of interaction with vitronectin as for treatment of the A27-vitronectin complex with 3M $MgCl_2$ to lead to recovery of >90% of the purified vitronectin. Furthermore, A27 affinity matrices may be reused in multiple cycles successfully.

The characterisation of the vitronectin prepared on A27 shows that its biochemical and biological activities remain intact.

Use of Immobilized Anti-Vitronectin Antibodies to Exhaustively Remove Vitronectin From Bovine Serum.

Figure 7:
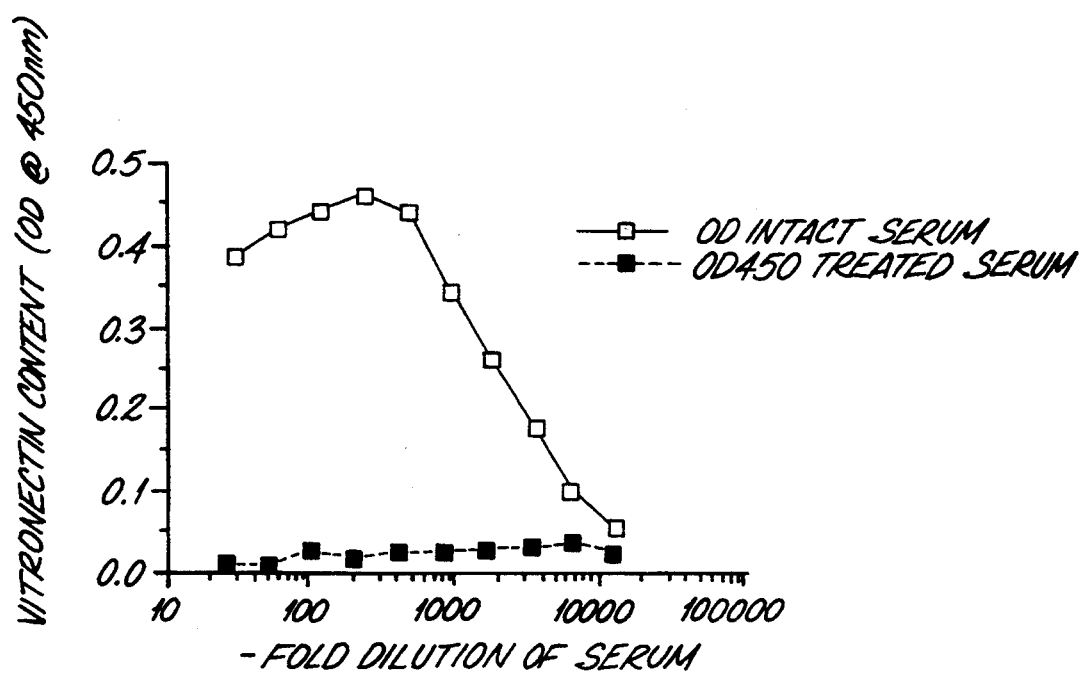

The bovine serum or plasma which is eluded from the anti-vitronectin affinity column has been exhaustively depleted of the vitronectin component. FIG. 7 shows that serum passed over A27-AFFIGEL is completely devoid of detectable vitronectin whereas considerable activity is detectable in the magnesium chloride eluate. The glass bead method of purification of vitronectin from bovine serum would be unlikely to exhaustively and selectively remove vitronectin from the serum in this way.

The recovery of purified vitronectin and efficiency of removal of vitronectin from bovine serum was determined as follows.

The concentration of vitronectin purified from a 40 ml sample of bovine serum was found to be 355 ug/ml. The total volume of purified material was 6.0 ml, and the total yield was 2.13 mg. In terms of the original 40 ml serum sample, this represents a yield of 53.25 ug/ml. The horizontal displacement in the titration curves in FIG. 8 was 1.5 $\log_2$. The starting concentration of the purified vitronectin in the assay was 1.55 ug/ml, and the starting dilution of the raw serum was 1/100. Therefore the concentration of vitronectin in the raw serum can be calculated as $1.55 \div 2^{1.5} \times 100 = 55$ ug/ml. Therefore the percentage yield of purified vitronectin from the raw serum $= 53.25 \div 55 \times 100 = 96.8\%$. The inability of this vitronectin-depleted serum to support cell attachment and growth on tissue culture polystyrene is described in Example 3.

EXAMPLE 3

Use of Immobilized Anti-Vitronectin and Antifibronectin Antibodies to Modify Surfaces, and the Importance of Orientation in Determining Whether Cell Colonization of a Surface is Improved or Inhibited by this Method Background.

Mammalian sera contain two major cell-adhesive proteins, fibronectin (alias cold insoluble globulin and LETS protein) and vitronectin (alias α-1 glycoprotein, serum spreading factor, epibolin and S-protein). Early experiments correlating the extent of cell adhesion and cell spreading with adsorption of fibronectin to the culture substratum from serum containing medium, suggested that fibronectin accounted for most of the adhesive/cell spreading activity in serum (Grinnell & Feld, 1982). This was supported by the inhibition of cell spreading in plasma-containing media by anti-fibronectin antibody (Grinnel & Phan, 1983) and the failure of some rumour cell lines to spread in serum-containing media depleted of fibronectin (Rajaraman et al. 1983). In contrast to these studies, circumstantial evidence suggests that under most common tissue-culture conditions, it is vitronectin that is the effective molecule for cell adhesion and spreading. Batches of foetal bovine serum prepared for tissue culture are frequently clotted at 4° C. which leads to considerable depletion of fibronectin (Knox & Griffiths, 1980). Hayman et al. (1985b) reported a range of 5 to 50 fold excess of vitronectin compared with fibronectin amongst different lots of tissue culture grade bovine serum. Knox & Griffiths (1980) fractionated sera from a number of different mammalian species and demonstrated higher cell attachment activities in the vitronectin peak compared to the fibronectin peak for all species tested. Federgreen & Stenn (1980) and Michl et al. (1983) reported successful cell spreading in media containing fibronectin- depleted serum. Other circumstantial evidence comes from similarities of attachment and spreading conditions required on vitronectin coated substrata and in serum-containing media, which differed from those on fibronectin coated substrata. These include sensitivity of cell spreading to cycloheximide (Knox & Griffiths, 1980), independence of cell spreading on cell-surface heparan sulphate (McInnes et al, 1987), level of $Ca^{2+}$ required for cell attachment (Edwards et al, 1987) and lack of sensitivity to antibodies blocking the activity of cell surface receptors for fibronectin (Neumeier & Reutter, 1985). Knox (1984) demonstrated that serum concentrations below 3% produced cell-spreading characteristic of that on fibronectin, whereas above 3%, cell spreading correlated with that on vitronectin. This author suggested that at serum concentrations above 3%, deposition of fibronectin onto the substratum may be inhibited by other serum proteins whereas that of vitronectin may be unaffected. This body of evidence in favour of vitronectin as the active attachment/spreading factor in serum-containing media is all of a circumstantial nature. In Example 3, we have used the technique outlined in Example 2 of purifying bovine vitronectin and of quantitatively and selectively depleting serum of vitronectin to study the role of vitronectin and fibronectin in the attachment of adherent animal cells to the biomaterial surface "tissue culture polystyrene". We have compared the adhesion of two very different cell types to purified vitronectin and fibronectin. We demonstrate conclusively that:

(1) the initial adhesion and spreading of fibroblasts and endothelial cells onto a hydrophilic biomaterial surface such as tissue culture polystyrene is absolutely dependent upon adsorption onto the polymeric surface of an adhesive glycoprotein such as vitronectin;

(2) even though each of these cells is capable of attaching to immobilised fibronectin it is serum vitronectin that is the only operative cell adhesion/-spreading molecule for both cell types when the cells are seeded in medium containing serum onto tissue culture polystyrene;

(3) this requirement for serum vitronectin cannot be replaced by the addition of soluble fibronectin to the culture medium, even at high concentration.

These results have implications for the design of biomaterial surfaces, both where the biomaterials are to be used for in vitro biotehnological applications (e.g. cell culture) and also where the biomaterials are to be used for implants where the application requires good attachment of the cells from the surrounding tissue. Previously the design of such biomaterials has been done on a somewhat empirical basis. Example 3 shows that as a suitability or otherwise of a polymeric surface for cell attachment is dependent upon the adsorption onto the surface of a population of proteins which may include cell adhesive glycoproteins, an improved design of biomaterial would be to have, as part of the polymeric surface, monoclonal antibodies that would specifically bind the desired biologically active proteins such as vitronectin or fibronectin. Monoconal rather than polyclonal antibodies would be preferred for such a purpose, as the antibody to be used could be selected for the epitope at which the antibody binds. Proteins such as fibronectin or vitronectin have multiple domains, each having specific biological effects. The monoclonal antibodies that are suitable for such a purpose would be those that bind the vitronectin or fibronectin with a suitably high affinity, and orient these proteins in such a configuration as for the cell attachment domain or domains to be available for recognition by cells. We show in Example 3 that certain of the monoclonal antibodies described in Example 1 and that bind to human fibronectin are not suitable for use as a component of a biomaterial surface where cell attachment is to be promoted, but two other monoclonal antibodies which react with human fibronectin (A35 and A9) are preferred for this purpose. Interestingly, the two monoclonal antibodies against fibronectin A35 and A9 react with the "heparin-binding region" at the carboxy terminal end of fibronectin but another monoclonal antibody which reacts with human fibronectin at this same region (A32 ) is not suitable for use as an immobilized monoclonal antibody to promote cell attachment and spreading.

Materials and Methods.
Cell Culture.

Primary cultures of bovine corneal (BCE) or aortal (BAE) endothelial cells were prepared from steer eyes or aortae as described by McAuslan et al. (1979). Cultures were maintained in McCoys 5A medium (Cytosystems, Australia) or medium 199 with Hanks Salts (Flow). The medium contained 10–20% FCS (Gibco), $10^{-5}$M thymidine, 100 units/ml penicillin, 100 ug/ml Streptomycin sulphate, 50 ug/ml Kannamycin and 5 ug/ml Fungizone. Cells were passage at 1:2–1:4 split ratio after disaggregation with trypsin/EDTA. Cells were discarded after 9–11 passages. BHK-21 fibroblast cells were maintained in medium 199 or Dulbecco's modification of Eagles salts (DMEM, Gibco) containing 10% tryprose phosphate broth (Flow), 10% FCS, penicillin and streptomycin. Tissue culture plasticware was from Nunc or Corning.

Removal of Fibronectin and Vitronectin From Serum.

Fibronectin was removed from batches of FCS using gelatin SEPHAROSE (Pharmacia) as follows. Five volumes of packed gelatin sepharose were washed with SFM and then scraped into 4 volumes of serum. This was left standing at room temperature for 1 hr with occasional stirring. The mixture was poured into a chromatography column and the serum drained off and stored at −20° C. Vitronectin was removed by affinity chromatography on the same MAb A27 affinity column used to purify vitronectin (see Examples 1 and 2 above). The affinity column was washed with SFM before application of serum. Fractions were collected and stored at −20° C. The absence of fibronectin or vitronectin was verified by coating ELISA plates with dilutions of stripped serum and testing for fibronectin or vitronectin with monoclonal antibodies as described above in Example 2. Where serum lacking both adhesive factors was required, fibronectin was removed before vitronectin. All samples were filtered through 0.22 um filters (Gelman) before use in tissue culture, and were used at concentrations compensating for dilution in affinity chromatography.

Cell Adhesion Assays

ASSAY 1. Use of Antibody Coating Onto Plastic For Presentation of Fibronectin or Vitronectin in Cell Adhesion Assay.

Bacteriological plates or dishes were coated with 10 ug/ml purified MAbs in PBS by incubation for 48 hr at 4° C. Negative controls were coated with non-specific mouse immunoglobulin of appropriate subclass, positive controls with PBS alone. The plates were blocked with 1% BSA in PBS for 1 hr at room temperature, washed once with blocking solution and then incubated with blocking solution containing 2 ug/ml fibronectin or vitronectin. (Positive controls were not blocked and received fibronectin or vitronectin in PBS, followed by the blocking step.). After 2 hr incubation with the fibronectin or vitronectin solution at room temperature, the plates were washed 3 times with SFM. Disaggregated BHK-21 cells (see Example 2) were added at $3-5 \times 10^5$/ml in SFM+1% BSA and incubated at 37° C. for 45 min or longer. After gently pipetting, samples of the culture supernatant were taken for cell counting in a haemocytometer. Percent cell adhesion was calculated as 100×[negative control count−experimental count]/negative count.

ASSAY 2. Standard Assay for Effect of Mabs on Cell Attachment to Adhesive Factors: Using Fibronectin or Vitronectin Coated Directly onto Plastic to Mediate Cell Adhesion: and Examining the Effect of Monoclonal Antibodies on Cell Attachment.

This assay was an adaptation of that described by Barnes et al. (1983). Dilutions of vitronectin or fibronectin in PBS were coated onto 35 mm bacteriological plastic dishes (Bunzel, Australia) or 25 well bacteriological plates (Sterilin) (2 ml and 1 ml respectively), by incubation for 2 hr at room temperature. Negative controls comprised coating with PBS alone. The coating solution was replaced with the same volume of 1% BSA in PBS for a further hour to block any unoccupied protein-binding sites. The plates were rinsed 3 times with the same volume of serum-free medium (SFM). Purified MAbs in SFM+1% BSA were added at a concentration of 62.5 ug/ml at room temperature for a further 2 hr. (Positive controls contained non-specific IgG.) One quarter of this volume of cell suspension in SFM+1% BSA was added to give final antibody concentration of 50 ug/ml and final cell concentration of $3-5 \times 10^5$/ml. The plates were incubated at 37° C. in a humidified CO$_2$ incubator (Forma) for 45-70 min, the number of non adherent cells was determined by the procedure outlined in section 1 above.

ASSAY 3. Modified Antibody Assay for Effect of Mabs on Cell Adhesion.

This assay is an extension to the assay described in ASSAY 1 above. After incubation with fibronectin or vitronectin, the plates were washed once with blocking solution and then incubated for 1 hr at 37° C. with the same MAb used for coating, at 10 ug/ml in blocking solution. The plates were then washed 3 times with SFM and incubated with cells as described in ASSAY 1 above.

Comparison of Fibronectin/Vitronectin Coating Plastic and to MAb.

Plates were coated with MAb as for the cell adhesion assay (described in ASSAY 1 above). After blocking, a range of concentrations of fibronectin or vitronectin in blocking solution were added. In parallel, plates which had been coated with PBS only, were incubated with the same concentration range of fibronectin/vitronectin in PBS. After 2 hr incubation, these plates were blocked with 1% BSA in PBS. At this point all plates were washed×3 with SFM. Some were then used for cell adhesion, while others were used for ELISA. In the ELISA, rabbit anti fibronectin/vitronectin was used (with pre-immune rabbit immunoglobulins as controls), and detected with peroxidase-conjugated swine anti-rabbit second antibody 1/1K (Dako). The conjugate solution contained 10% FCS and 10 ug/ml normal mouse IgG to reduce background. The ELISA was done as described above for hybridomas screening. Aliquots of the final reaction product were transferred to 96-well plates for reading on the plate reader.

Measurement of Dissociation Rates of Fibronectin From Coated MAbs.

Fibronectin was labelled with $^{125}$I (Amersham) using the chloramine T method (Stahli et al. 1983). This was added to cold fibronectin to give 100,000 counts per minute per ml (approximately 1:8000 hot:cold fibronectin). Antibody coating and fibronectin (2 ug/ml) incubation were carried out as described for ASSAY 1 above. SFM+1% BSA containing either the same MAb at 10 ug/ml; cells at $3 \times 10^5$/ml; both additions, or neither, was added and the plates were incubated at 37° C. At various time intervals the amounts of fibronectin bound and free were determined. Each treatment/time combination was duplicated. $^{125}$I was counted from the supernatants directly. Surface-bound material was released by incubation with 0.03% trypsin (Gibco) in Ca$^2$ and Mg$^2$+free PBS overnight, followed by addition of SDS to 3.3% (w/v) and incubation at 37° C. for a further 2 hr. The supernatant was then removed quantitatively and counted. Percent dissociation was calculated as 100×free count/free+bound counts.

Assay of Cell Adhesion to Human Fibronectin Using Coated Monoclonal Antibodies to Present Fibronectin From Raw Plasma Nunc maxisorp ELISA plates or Flow bacterial grade 96-well culture plates (No. 76-232-05) were coated with purified monoclonal antibody A35 at 20 ug/ml in 50 ul PBS per well for 3 days at 4° C. As negative controls a bovine fibronectin specific antibody (A22) and a bovine vitronectin specific antibody (A27) were similarly coated. After removal of the coating solution, dilutions of raw human plasma were added to the wells and incubated at room temperature for 2 hrs. Cell adhesion was measured by adding BHK-21 hamster kidney cells to each well. After incubation for 1 hr at 37° C. the extent of cell adhesion was measured by fixing and staining adherent cells with methylene blue by the method of Oliver et al (1989).

In parallel, the amount of fibronectin bound from the plasma dilutions to A35 was estimated by ELISA dose-response curves using biotin labelled monoclonal antibodies A9,A32 or A14 and purified fibronectin in parallel. These antibodies bind to sites on fibronectin remote from that of A35. A9 and A32 bind to the heparin-binding region of fibronectin and A14 to the cell-binding region (see Example 3).

Determination of Binding of Monoclonal Antibodies to Human Fibronectin and to Fragments of Human Fibronectin:

ELISA trays were coated with 5 ug/ml human fibronectin or the same concentration of bovine fibronectin, then the trays blocked and incubated for 2 hr at room temperature with the monoclonal antibodies. Three concentrations of monoclonal antibodies, 0.1 ug/ml, 1 ug/ml and 10 ug/ml were used. Bound monoclonal antibodies were detected by incubation with $^{125}$I-labelled goat anti-mouse IgGs (300,000 cpm/50 ul in each well, made up in ELISA wash buffer but additionally containing a 0.002 dilution of unlabelled goat anti-mouse IgGs antiserum).

Three fragments from human fibronectin were used to coat ELISA trays as follows:
(1) the 30,000 dalton "gelatin-binding region" was generated by trypsin cleavage (as in Pierschbacher, M D, Hayman, E G, and Ruoslahti, E, 1981, Cell 26, 259-267);
(2) the 40,000 dalton "heparin-binding region" from the carboxy-terminal end of fibronectin was generated by cleavage with α-chymotrypsin; and
(3) the 120,000 dalton cell attachment region was generated by cleavage with α-chymotrypsin.

These fragments were coated at 2.5 ug/ml and at 5 ug/ml for a 24 hr period. Monoclonal antibodies (1 ug/ml or 10 ug/ml) were incubated with the immobilized fragments for 2 hr at room temperature, then the bound monoclonal antibodies were detected as described above.

Results

Determination of crossreactivity of monoclonal antibodies to human fibronectin and identification of epitopes recognized by A9, A35 and A32 to fragements of human fibronectin.

Figure 9:
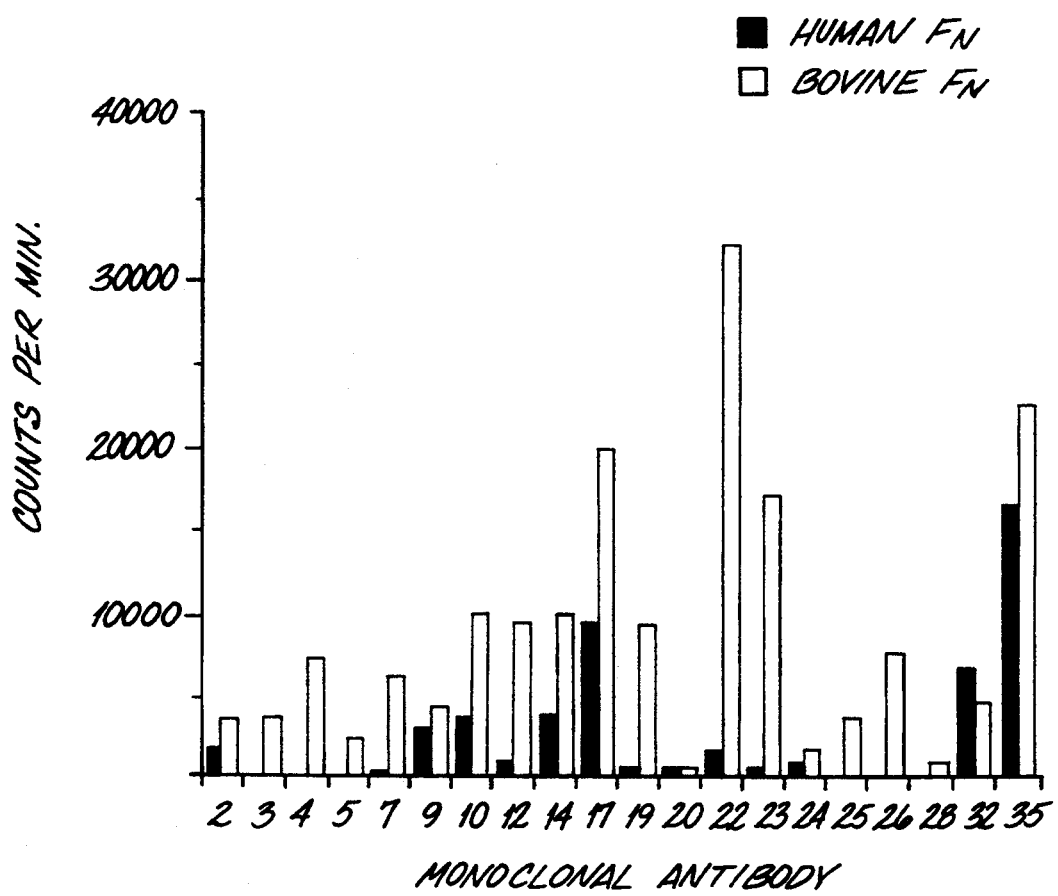

FIG. 9 shows the crossreactivity of the panel of anti-fibronectin monoclonal antibodies (as described in Example 1) with human fibronectin. It is clear that antibodies A35, A9, A32, A17, A14 and A10 bind to human fibronectin and also to bovine fibronectin. Of these monoclonal antibodies, A17, A14 and A32 were immobilized onto the cell culture substratum via antibody (see further details within this Example 3).

The crossreactivity of A35, A9 and A32 with three fragments from human fibronectin was tested. These fragments were:
(1) the 30,000 dalton "gelatin-binding region" was generated by trypsin cleavage (as in Pierschbacher, M D, Hayman, E G, and Ruoslahti, E, 1981, Cell 26, 259-267);
(2) the 40,000 dalton "heparin-binding region" from the carboxy-terminal end of fibronectin was generated by cleavage with α-chymotrypsin; and
(3) the 120,000 dalton cell attachment region was generated by cleavage with α-chymotrypsin.

FIGS. 10 & 11 show that A35, A9 and A32 each reacted specifically with the heparin-binding fragment from the carboxy terminal end of the fibronectin chain. Cell Growth in Media Depleted of Fibronectin or Vitronectin.

To compare the effects of fibronectin and vitronectin in serum-containing medium, BHK-21 fibroblast cells and BCE cells were grown in media selectively depleted of these molecules. Cell monolayers wee disaggregated and treated with soy bean trypsin inhibitor as for adhesion experiments. They were then seeded into a 24-well tissue culture plate (Costar) at the rate of $1 \times 10^5$ BHK or $7 \times 10^4$ BCE per well in 1 ml of growth medium containing either 20% whole FCS or 20% FCS stripped of fibronectin or vitronectin, or SFM. Treatments were set up in triplicate. Cultures were examined at 3.5 hr and daily thereafter. Control wells contained the various media without cells.

At 3.5 hr cells of both types were well spread in media containing whole serum or serum stripped of fibronectin. In contrast, in both SFM and medium containing serum stripped of vitronectin, cells of both types were poorly adhered and very rounded. The appearance of the cells at 24 hr was observed and both cell types showed normal adherence and growth with medium lacking fibronectin. In medium lacking vitronectin and in SFM cells tended to be clumped and poorly adhered, particularly BHK-21 cells. Longer incubation did not change the relative appearance of the cells. BAE cells performed essentially as BCEs. A second growth experiment was designed to ascertain the concentrations of vitronectin or fibronectin required, either precoated on the substrate, or included in the medium, to support normal cell adhesion and growth. Tissue culture plates (24-well) were coated with vitronectin or fibronectin at concentrations of 0, 1, 2.5, or 5 ug/ml in PBS (0.5 ml per well), at 37° C. for 2 hr. After thorough washing of the plates with SFM, cells were seeded at the rate of $1 \times 10^5$ BHK-21 or $6 \times 10^4$ BCE per well in 1 ml of medium containing 20% serum stripped of both fibronectin and vitronectin: Thus the only exogenous adhesive factors present were those coated on the substrate. A second set of plates were not pre-coated but were seeded with the same cell concentration in medium containing 20% serum stripped of both vitronectin and fibronectin and then supplemented with either of these molecules at concentrations ranging from 1 ug/ml to 50 ug/ml. In these cases exogenous adhesive factors were present in the overlying medium. Control cultures were set up in medium containing 20% whole serum. Cultures were observed daily. The relative amounts of fibronectin and vitronectin which adsorbed to the tissue culture wells were assayed by ELISA before and after coating, as described in Materials and Methods for bacteriological plates. The mean percentage adsorption of vitronectin for the coating concentration range 1-5 ug/ml war 74.3%±3.1 (5% confidence interval). For fibronectin over the same range the mean percent adsorption was 86.8%+2.9 (5% confidence interval). These vaues are similar to those observed for coating to bacteriological dishes, with fibronectin showing a slightly higher absorption efficiency than vitronectin.

The appearance of the cells at 24 hr was observed. Cells of both types had a very poor appearance in medium lacking both factors. Adhesion, spreading and growth were not improved by the addition of fibronectin to the overlying medium, in the concentration range up to 50 ug/ml. Conversely wells that were precoated with fibronectin concentrations at and above 2.5 ug/ml ($1.1 \times 10^{-11}$M) exhibited normal adhesion, spreading and growth. In contrast to the situation with fibronectin, vitronectin was equally efficient in promoting normal cell adhesion, spreading and growth whether precoated or added to the medium. In either case vitronectin was effective at concentrations at and above 2.5 ug/ml ($3.6 \times 10^{-11}$M).

This growth experiment demonstrated quite clearly that for these two cell types fibronectin could only be used as an adhesive molecule if it was precoated on the substratum, and that it could not be recruited from the serum-containing medium. The reason for this difference was demonstrated by comparing the amount of vitronectin and fibronectin coated on a 96-well tissue culture plate (Corning) in PBS compared with PBS containing 10% FCS (stripped of both molecules). Serial 2.2-fold dilutions of fibronectin or vitronectin starting from 10 ug/ml in either diluent, were added to duplicate wells of a 96-well plate. After 2 hr at 37° C. the plate was blocked with 1% BSA in PBS for 1 hr at 37° C. Adsorbed fibronectin and vitronectin were detected by ELISA with MAb A12 and A27 at 1 ug/ml. The relative efficiency of coating in the presence of serum was estimated as the percentage of ELISA absorbance in the absence of serum. The results are shown in Table 5. It is clear that while vitronectin could still adsorb in the presence of serum to a level of 50% of that achieved in PBS, the binding of fibronectin was reduced by as much as 97% in the presence of other serum

TABLE 5

The efficiency of coating vitronectin and fibronectin in the presence and absence of other serum proteins.

| (a) Vitronectin | Coating concentration ug/ml | | | | | | | |
|---|---|---|---|---|---|---|---|---|
| | 10 | 4.54 | 2.07 | 0.94 | 0.43 | 0.19 | 0.09 | 0.04 |
| Coating in PBS | >2[1] | >2 | >2 | 1.58 | 0.98 | 0.48 | 0.23 | 0.1 |
| Coating in PBS + 10% SS[2] | >2 | >2 | >2 | 1.05 | 0.54 | 0.22 | 0.11 | |
| | 0.06 | | | | | | | |
| % coating in SS vs coating in PBS | | | | 66.4 | 55.1 | 45.8 | 47.8 | |

| (b) Fibronectin | Coating concentration ug/ml | | | | |
|---|---|---|---|---|---|
| | 10 | 4.54 | 2.07 | 0.94 | 0.43 |
| Coating in PBS | | 1.42 | 0.65 | 0.24 | 0.11 |
| Coating in PBS + 10% SS | 0.08 | 0.04 | 0.02 | 0.0 | 0.0 |
| % coating in SS vs coating in PBS | <4.0 | 2.8 | 3.1 | | |

[1]Absorbances as for Table 1. MAb A27 and A12 were used at 1 ug/ml to detect vitronectin and fibronectin respectively. Absorbance values are corrected for non specific antibody (normal mouse IgG1).
[2]SS = serum stripped of both fibronectin and vitronectin proteins. This means that in medium containing 50 ug/ml fibronectin (well above the expected level in most culture media) a maximum coating corresponding to 1.5 ug/ml in PBS could be expected. This is below the critical limit determined from the growth experiments.

Comparison of Binding between antigen and antibody, when either antigen was immobilized, or antibody was immobilized.

These results are shown in Table 6. For most antibodies, reasonable levels of antigen were bound to coated antibody from 2 ug/ml fibronectin and 1 ug/ml vitronectin respectively. The exception was A25 which showed very poor binding of fibronectin to coated antibody. For this reason A25 was not used in any of the immobilized antibody cell adhesion assays.

Use of anti-vitronectin of anti-fibronectin antibodies to bind vitronectin or fibronectin and enhanced cell attachment and growth to the modified surface.

Figure 12:
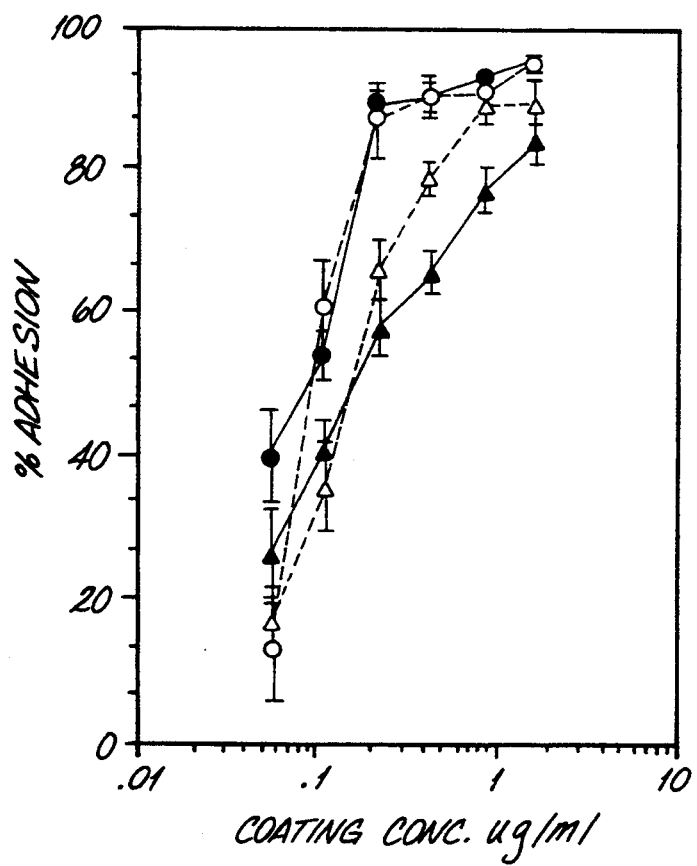

Some antibodies coated on the plastic surface, as described for ASSAY 1, could bind fibronectin or vitronectin to maintain stable cell adhesion and spreading for at least 24 hr. Their performance as a substrate for presenting a range of concentrations of these adhesive molecules to cells was compared with that of bacteriological plastic. The results are shown in FIG. 12. Very little difference was observed between the adhesion of cells to the higher concentrations of fibronectin presented on A22 or on plastic. At the lowest concentration used (0.06 ug/ml) fibronectin presented on A22 produced significantly greater cell adhesion than that on plastic. A similar trend was observed on vitronectin. At the higher vitronectin concentrations, plastic appeared to be a little more efficient than A27 at presenting vitronectin for cell adhesion, whereas at the lower concentrations the binding curves crossed over and

TABLE 6

Binding of FN/VN to coated antibodies and of antibodies to coated FN/VN.

| MAb | FN/VN bound to coated antibody[1] | Antibody titre on coated FN/VN[2] |
|---|---|---|
| A2 | 1.40 | 8 |
| A3* | 1.57 | 1 |
| A4 | 0.82 | 8 |
| A5 | 0.34 | <1 |
| A7 | 0.58 | 1 |
| A9 | 0.76 | 2 |
| A10 | 0.85 | <1 |
| A12 | 1.78 | 4 |
| A14 | 1.53 | 12 |
| A17 | 1.64 | 16 |
| A19 | 1.43 | 12 |
| A20* | 1.59 | <1 |
| A22 | 1.62 | 16 |
| A23 | 1.69 | 16 |
| A24* | 1.21 | 1 |
| A25* | 0.21 | 16 |
| A26 | 1.37 | 4 |
| A28* | 1.61 | <1 |
| A32 | 1.04 | 16 |
| A35 | 1.72 | 32 |
| FN 0.5 ug/ml[3] | 1.32 | |
| FN 0.25 ug/ml[3] | 0.79 | |
| A18 | 1.21 | 32 |
| A27 | 1.43 | 32 |
| VN 0.5 ug/ml[3] | 1.02 | |
| VN 0.25 ug/ml[3] | 0.72 | |

[1]Antibody coated at 10 ug/ml + FN at 2 ug/ml or VN at 1 ug/ml (Assay 1 conditions). ELISA absorbance at 450 nm, corrected for non-specific mouse antibody and non-specific rabbit antibody. Means of duplicate readings.
[2]Highest two fold dilution of FN/VN coating (starting from 10 ug/ml) in Dynatech ELISA plates giving maximal binding of monoclonal antibody at 1 ug/ml.
[3]Control wells coated with PBS and then FN/VN at the given concentrations in PBS, before the blocking step.
*Major discrepancy between antigen/antibody binding in the two assays.

vitronectin on A27 produced more cell adhesion than on plastic. These results were reflected in the relative amounts of fibronectin and vitronectin bound to antibodies or plastic, measured by ELISA (Table 7). Absolute values cannot be compared between plastic and antibody since the effect of binding of antigen to plastic, on antibody reactivity, is not known. The relative values however can be compared between the different dilutions of antigen.

Figure 13:
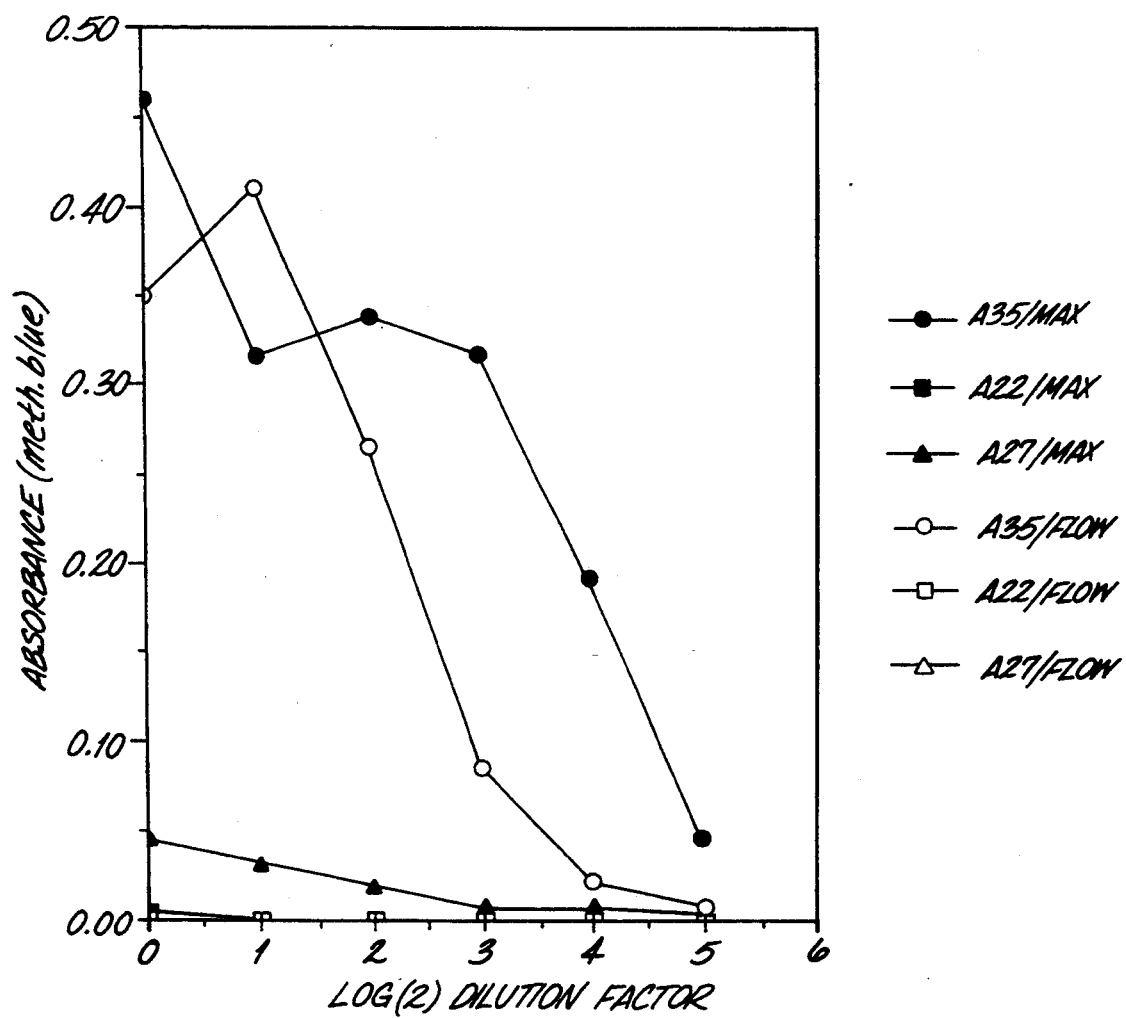

Other monoclonal antibodies, when immobilized onto a plastic surface as described for ASSAY 1, could bind fibronectin or vitronectin, but the bound fibronectin or vitronectin failed to present a surface that was suitable for cell attachment and spreading. In this assay (Table 8) five antibodies were identified as inhibitory (A25 not included); four of these were also inhibitory in ASSAY 2 but the effect was only detectable up to 1½ hr incubation. Extended incubation of ASSAY 1 tended to increase the inhibitory effect such that after 24 hr at 37° C., there was no significant adhesion at all to fibronectin or vitronectin coated on these 5 antibodies. Conversely, cells incubated for 24 hr on fibronectin or vitronectin coated on A12, A22, A23, A35 or A27, showed approx. 100% adhesion and were well spread. In another experimental series, monoclonal antibodies were immobilised and used to adsorb fibronectin from raw human plasma, then the suitability of the surface for the attachment of fibroblasts was tested. FIG. 13 shows that with both maxisorp and Flow plates, specific cell adhesion was observed only with human plasma dilutions on A35, and not with the bovine-specific and fibronectin and anti vitronectin antibodies A22 and A27 respectively. Specific cell adhesion was also seen when A9 was used to coat the plates and human plasma and cells applied by the same method (data not shown).

Figure 14:
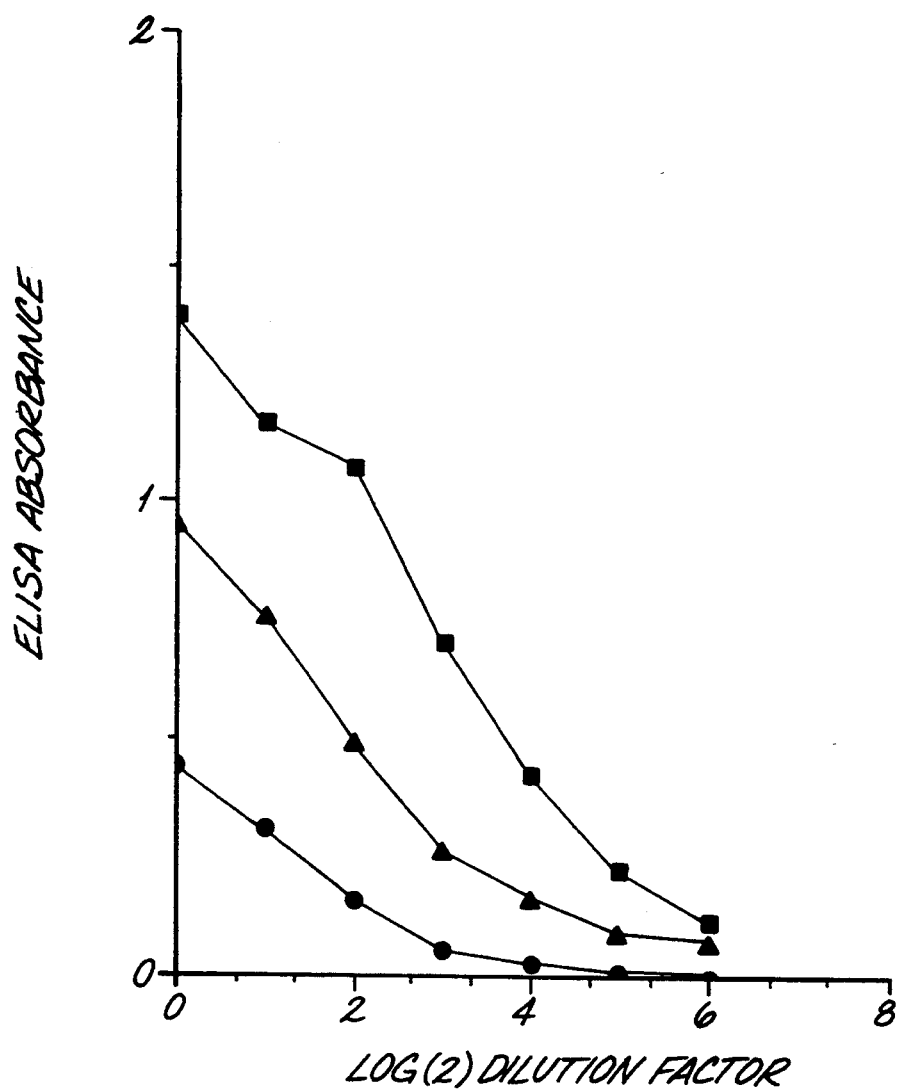

FIG. 14 shows monoclonal antibody binding titration curves with the same plasma sample as in FIG. 13 using the three different monoclonal antibodies A9, A32 or A14 for detection. Although not shown, the titration curves can be quantitated by comparison with a purified fibronectin standard.

These results show that monoclonal antibodies can be used to present adhesive molecules in different orientations to either promote cell adhesion or to prevent it. Similar efficiencies were observed, with the present set of conditions, between coating fibronectin and vitronectin on antibodies compared with on plastic. Grinnel & Feld (1982), however, have described avid coating of fibronectin to bacteriological plastic at the expense of cell-adhesive activity, and Lewandowstria et al. (1988) have described different plastic binding characteristics of different fibronectin fragments. In contrast, coated antibody molecules would present the antigen homogenously with a specific orientation. We investigated only one concentration and method of initial antibody coating. It may be possible to increase the efficiency of cell adhesion to low concentrations of fibronectin or vitronectin by manipulating the initial antibody coating conditions.

This method of using immobilized Mabs to specifically adsorb adhesive glycoproteins and so present an active surface for cell colonisation would be particularly useful where there is a preference to use serum or plasma material from the same patient as the source of the adhesive proteins. For this reason, a surface including monoclonal antibodies A35 or A9 which react with human fibronectin may be preferred for applications such as that of preseeding vascular grafts with endothelial cells prior to implantation (Herring, et al., 1978). By presenting a surface consisting of immobilized Mab, the adhesive glycoproteins may be selectively and quickly adsorbed onto the surface from the serum or plasma. We have shown here that fibronectin is not effectively adsorbed onto plastic surfaces from serum, due to competition for the binding sites on the plastic from other serum proteins, and so as to achieve an active fibronectin concentration for cell attachment, purified fibronectin must be used. The use of immobilized Mab enables fibronectin to be adsorbed onto the surface from serum or plasma, to give sufficiently high concentration as for cell attachment. For clinical use, there is the obvious advantage that the patient's own plasma or serum may be used to coat the surface with adhesive proteins, in a rapid procedure that does not require purification steps.

The method may be extended to functions of fibronectin and vitronectin other than that of cell adhesion. Monoclonal antibodies reactive with particular domains on fibronectin or vitronectin molecules, could be used to present these molecules in a manner to uniformly

TABLE 7

Coating of fibronectin and vitronectin to plastic or antibody

| Substrate | 0.06 | 0.12 | 0.25 | 0.50 | 1.00 |
|---|---|---|---|---|---|
| | Vitronectin coating concentration ug/ml | | | | |
| Plastic | 0.31 | 0.48 | 0.72 | 1.02 | 1.29 |
| A27 | 0.81 | 0.98 | 1.13 | 1.25 | 1.43 |
| | Fibronectin coating concentration ug/ml | | | | |
| Plastic | 0.21 | 0.39 | 0.62 | 0.92 | 1.24 |
| A22 | 0.75 | 0.96 | 1.12 | 1.27 | 1.30 |

TABLE 8

Cell adhesion in the standard assay and antibody coating assay.

| MAb | ASSAY 2[1] | Percent adhesion ASSAY 1[2] |
|---|---|---|
| A2 | 93.2 | 92.7 |
| A3 | 94.0 | 88.6 |
| A4 | 94.8 | 89.2 |
| A5 | 95.2 | 83.4 |
| A7 | 95.6 | 86.8 |
| A9 | 96.0 | 89.0 |
| A10 | 95.6 | 96.5 |
| A12 | 94.8 | 99.6 |
| A14 | 80.3* | 72.8* |
| A17 | 69.8* | 79.5* |
| A19 | 96.4 | 97.6 |
| A20 | 93.2 | 93.3 |
| A22 | 96.4 | 98.8 |
| A23 | 89.5 | 99.2 |
| A24 | 78.3* | 65.7* |
| A25 | 81.1* | Not done |
| A26 | 95.6 | 99.4 |
| A28 | 92.0 | 93.5 |
| A32 | 96.4 | 70.0* |
| A35 | 94.8 | 98.2 |
| Nm control[3] | 95.2 | 0.0 |
| PBS control[4] | NA | 87.6 |
| A18 | 42.5* | 5.3* |

TABLE 8-continued

Cell adhesion in the standard assay and antibody coating assay.

| MAb | ASSAY 2[1] | Percent adhesion ASSAY 1[2] |
|---|---|---|
| A27 | 87.5 | 92.2 |
| Nm control[3] | 88.7 | 0.0 |
| PBS control[4] | NA | 91.9 |

[1]Percentage of cells added which were adhered after 45 min FN/VN coated at 2 ug/ml; antibodies at 50 ug/ml.
[2]Percentage of cells added which were adhered after 1.5 hr MAbs coated at 10 ug/ml followed by FN/VN at 2 ug/ml.
[3]Non-specific mouse 1 gG used in place of MAb.
[4]Plates coated with PBS in place of MAb, followed by 2 ug/ml FN/VN in PBS.
*Significantly reduced adhesion compared to Nm control (standard assay) or PBS control (antibody coating assay). P < 0.05, Student Neuman Keuls test. (Means of 9 estimations).
NB These two assays were performed on different days.

block or enhance particular functions, such as binding to collagens or proteoglycans. The method may also be extended to the use of specific Mabs for the presentation of other factors required for he cell colonisation of a surface, such as the presentation of growth factors that cells such as endothelial cells may require or prefer for cell growth and colonisation. It is obvious that such applications may have far reacting consequences in the biomaterials field.

Use of immobilized antibodies in improved cell attachment immunobioassays for attachment factors.

The rationale behind using ASSAY 3 was that for divalent molecules such as fibronectin, the molecule could be anchored to an inhibitory antibody substrate by one arm and still have the second arm free to mediate cell adhesion. If antibody is layered on top, hopefully both arms of the molecule will be antibody bound. To test this, all three types of adhesion assay were performed on the same day so that their relative efficiencies could be directly compared. This was only done with fibronectin antibodies as vitronectin is monovalent and ASSAY 1 with A18 had already reduced cell adhesion to a level not significantly different from 0 (Table 8). The results of the ASSAY 3 are shown in Table 9. Each inhibitory antibody showed an increased effect in the ASSAY 3 compared to either the ASSAY 2 or ASSAY 1 A7 was additionally identified as an inhibitory antibody by ASSAY 3. Antibodies displaying no inhibitory activity (represented by A22 and A23 in Table 8) showed excellent adhesion in both ASSAYS 1 and 3.

To demonstrate that the increased inhibitory effects observed with the ASSAY 3 were not due to simple dissociation of the fibronectin from the coated antibody, dissociation rates of $^{125}I$ labelled fibronectin from antibodies A17 and A23 were compared under conditions mimicking those of the cell adhesion assay. The results are shown in Table 10. The dissociation rates of $^{125}I$ fibronectin from the two antibodies were very similar. In both cases the presence of MAb in the fluid phase of the reaction (mimicking assay 3) had not effect on dissociation rates. The presence of cells considerably increased fibronectin dissociation, but the levels were still similar for both antibodies. This indicates that the inhibitory effects shown in the cell assays 1 and 3 were genuine, and not due to differential dissociation rates of fibronectin from immobilized antibody. The amounts of fibronectin initially bound to A17 and A23 were very similar (ELISA results in Table 6) and also similar to the amounts bound to A14, A22, A24 and A32. Lower amounts were bound to A7 (Table 6) and one might argue that this initial lower binding concentration might result in a reduction in cell adhesion. The cells adhered as

TABLE 9

Comparison of cell adhesion to fibronectin in the three adhesion assays

| MAb | ASSAY 2 | Percent adhesion[1] | |
|-----|---------|---------|---------|
|     |         | ASSAY 1 | ASSAY 3 |
| A7  | 91.5    | 87.7    | 63.8*   |
| A14 | 86.0    | 70.1*   | 32.2*   |
| A17 | 74.2*   | 37.1*   | 18.2*   |
| A22 | 96.2    | 97.9    | 99.6    |
| A23 | 97.2    | 96.3    | 95.3    |
| A24 | 66.8*   | 74.9*   | 28.1*   |
| A32 | 96.0    | 66.1*   | 30.3*   |

TABLE 9-continued

Comparison of cell adhesion to fibronectin in the three adhesion assays

| MAb | ASSAY 2 | Percent adhesion[1] | |
|-----|---------|---------|---------|
|     |         | ASSAY 1 | ASSAY 3 |
| PBS control | 95.1 | 94.7 | 95.4 |

[1]Percentage of cells added which were adhered after 1 hr. Means of 9 estimations. Assay conditions given in Materials and Methods. FN used at 2 ug/ml throughout.
*Significantly reduced adhesion compared to PBS controls. Student Neuman Keuls test $P < 0.05$.

TABLE 10

Dissociation of $^{125}I$ fibronectin from MAbs coated on plastic wells

| Treatment[2] | Percent dissociation[1] at | | |
|---|---|---|---|
|  | 1 hr | 4 hr | O'night |
| (a) A17 |  |  |  |
| [SFM + 1% BSA] | 14.7 | 15.8 | 23.4 |
| SFM + cells | 20.7 | 27.4 | 54.4 |
| SFM + MAb A17 | 10.5 | 22.7 | 27.0 |
| SFM + MAb + cells | 17.9 | 37.0 | 57.3 |
| (b) A23 |  |  |  |
| [SFM + 1% BSA] | 14.8 | 23.1 | 28.2 |
| SFM + cells | 22.2 | 34.7 | 61.2 |
| SFM + MAb A23 | 15.0 | 25.5 | 31.3 |
| SFM + MAb + cells | 19.2 | 36.3 | 67.0 |

[1]Percentage of bound label (under antibody coating assay conditions) dissociated after incubation for the indicated times at 37° C. Means of duplicates.
[2]Dissociation carried out in SFM + 1% BSA with or without the same MAb at 10 ug/ml or BHK-21 cells at $3 \times 10^5$/ml.

well, however, to fibronectin coated on antibody A7 as they did to fibronectin coated on plastic (Table 8 and Table 9, columns 1 and 2). Thus the observed inhibition in the ASSAY 3 (Table 9, column 3) is likely to be genuine. Since the three different assays were performed concurrently, dissociation rates would have been similar in each case.

The results described show that immobilized monoclonal antibodies can be used to present adhesive molecules in different orientations, such as to either promote cell adhesion or to prevent it. The results comparing the detection of inhibitory Mabs in ASSAY 2 vs. ASSAY 3 indicate that this method forms the basis of an immunobioassay of the adhesive activity of fibronectin or vitronectin which is more sensitive (see results with Mab A7 for example) and has a more persistent endpoint than the standard format for such assays (ASSAY 2). There is increasing interest in the reactivity of extracellular matrix molecules, such as fibronectin and vitronectin, with cells and with each other. In certain pathological conditions errors in production and assembly of matrix molecules may occur or destruction of basement membranes and connective tissue (Timpl & Dziadek, 1986). For example in some cancer patients different molecular weight forms or aggregation states of fibronectin may occur (Barlati et al. 1986); Vuillard et al. 1988). Little is known of the functional significance of such changes. Solid phase domain specific monoclonal antibodies could be used in a sensitive specific assay for the functional state of particular antigens in a manner similar to that presently described for cell adhesion, in parallel with quantitative assays.

BIBLIOGRAPHY

Akama, T. et al. 1986, J. Biochem, 100, 1343–1351;
Baetscher, M. et al. (1986) J. Cell Biol., 103, 369–378;
Barlati, S. et al. (1986) Front. Matrix Biol., 11, 174–182;
Barnes, D,W. et al. (1983) PNAS (USA), 80, 1362–1366;

Barnes, D. W. et al. (1985) J. Biol Chem., 260, 9117–9122;
Dahlback, B. and Podack, E. R. (1985) Biochem, 24, 2368–2374;
Edwards, J. G. et al. (1987) J. Cell Sci. 87, 657–665;
Erickson, P. F. et al. (1982) J. Immunol Methods 51, 241–249;
Federgreen, W. & Stenn, K. S. (1980) J. Invest Dermatol. 75, 261–263;
Gospodarowicz, D & Lui, G-M. (1981) J. Cell Physiol, 109, 69–81;
Gospodarowicz, D. et al. (1980) PNAS (USA) 77, 4094–4098;
Grinnell, F & Feld, M. K. (1982) J. Biol Chem. 257, 4888–4893;
Grinnell, F & Phan, (1983) J. Cell Physiol. 116, 289–296;
Hawkes, R. et al. 1982, Anal. Biochem. 119, 142–147;
Hayashi, M. et al. 1985, J. Biochem. 98, 1135–1138;
Hayman, E. G. et al. (1983) PNAS USA 80, 4003–4007, 1983;
Hayman, E. G. et al. (1985a) Exp. Cell Res. 160, 245–258;
Hayman, E. G. et al. (1985b) J. Cell Biol. 100, 1948–1954;
Herring, et al. (1978) Surgery, 84, 498–504;
111, C. R. and Ruoslahti, E. (1985), J. Biol Chem. 260, 15610–15615
Knox, P. & Griffiths, S. (1980) J. Cell Sci. 46, 97–112;
Knox, P. (1984) J. Cell Sci. 71, 51–59;
Laemmli, U. K. (1970) Nature 227, 680–685;
Lewandowstria, K. et al. (1988) FEBS Letts., 237, 35–39
Lowry, O. H. et al. (1951) J. Biol. Chem, 193, 265–275;
McAuslan, B. R. et al. (1979) J. Cell Physiol, 100, 87–94;
McInnes, C. et al. (1987) J. Cell Sci, 88, 623–629;
Mayes, E. V. (1984) Immunoaffinity purification of protein antigens. In Methods of Molecular Biology, 1. Proteins, (ed. J. M. Walker), pp 13–20. Humana Press, Clifton N.J.;
Michl, J. et al. (1983) Cell Biochem & Function, 1, 87–91;
Neumeier, R. & Reutter, W. (1985) Exp. Cell Res. 160, 287–296;
Neyfakh, A. A. et al. (1983) Exp. Cell Res. 149, 387–396;
Oliver, M. N. et al. (1989) J. Cell. Sci. 92, 513–18;
Preissner, K. T. et al. Biochem. J. 231, 249–355;
Rajaraman, R. et al. (1983) Exp. Cell Biol. 51, 9–18;
Silnutzer, J. and Barnes, D. W. 1984 Biochem Biophys Res. Commun 118, 339–343;
Silnutzer J. E. et al. 1985, In vitro Cell and Develop. Biol, 21, 73–78;
Sorensen, K. & Brodbeck, U. (1987) Experimentia 42, 161–163;
Stahli, C. et al. (1983) Meth. Enzymol., 92, 242–253;
Steele, J. G. et al. (1985), Molecular Immunology 22, 1061–1072;
Timpl, R. & Dziadek, M. (1986) Int. Rev Exp. Pathol,m 29, 1–112;
Tomasini, B. R. and Mosher, D. F. (1986), Blood, 68, 737–742;
Underwood, P. A. & Bean, P. (1988) J. Immunol. Methods, 107, 119–128;
Underwood, P. A. et al. (1983) J. Immunol. Methods, 60, 33–45;
Underwood, P. A. (1982) J. Gen. Virol., 62, 153–169;
Underwood, P. A. (1985) J. Immunol. Methods, 85, 309–323;
Underwood, P. A. and Bennett, F. A. (1989) J. Cell. Sci. 93, 641–649;
Vuillard, L. et al. (1988) FEBS Letts, 238, 5–8;

We claim:

1. A monoclonal antibody A27 which specifically binds bovine vitronectin such that the bound vitronectin retains its cell binding activity, the monoclonal antibody being produced by hybridoma cell line ECACC 89011102.

2. A monoclonal antibody A18 which specifically binds bovine vitronectin such that the cell binding activity of the vitronectin bound to the antibody is lost, the monoclonal antibody being produced by hybridoma cell line ECACC 89011103.

3. A monoclonal antibody, designated A32, which specifically binds to fibronectin wherein the monoclonal antibody designated A32 is produced by hybridoma cell line with ECACC accession number 91090301.

4. A biomaterial comprising a support, wherein the support is coated with a monoclonal antibody selected from the group consisting of monoclonal antibody A18, monoclonal antibody A27, monoclonal antibody A35 and mixtures thereof, the monoclonal antibody being orientated such that an antigen binding region of the monoclonal antibody is remote from the support, the monoclonal antibody designated A18 being produced by hybridoma cell line with ECACC accession number 89011103, the monoclonal antibody designated A27 being produced by hybridoma cell line with ECACC accession number 89011102 and the monoclonal antibody designated A35 being produced by hybridoma cell line with ECACC accession number 89113011.

5. A biomaterial as claimed in claim 4 in which the monoclonal antibody is A35.

6. A biomaterial as claimed in claim 4 in which the monoclonal antibody is A27.

7. The biomaterial as claimed in claim 4 in which the support is a polymer selected from the group consisting of agarose, polyacrylamide, polyvinyl alcohol, polyester, polystyrene, polytetrafluoroethylene, poly(ethylene terephthalate), polyurethane, silicon rubber and poly(-hydroxyethyl methacrylate).

8. A device for use in in vitro cell culture or for the removal of vitronectin from bovine serum and plasma, the device comprising a cell contacting surface which is coated is coated with monoclonal antibody A18 or A27, wherein the monoclonal antibody A18 and A27 are produced by hybridoma cell lines designated ECACC 89011103 and 89011102, respectively, the monoclonal antibody being orientated such that the vitronectin binding region of the monoclonal antibody is remote from the surface.

9. The device as claimed in claim 8 in which the monoclonal antibody is A27.

10. The device as claimed in claim 8 in which the cell contacting surface is an affinity chromatography matrix.

11. A method of removing vitronectin from bovine plasma or serum containing vitronectin, the method comprising the sequential steps of:
   1) providing monoclonal antibody A18 or A27 on a solid support such that the vitronectin binding region of the monoclonal antibody is remote from the solid support;
   2) contacting said solid support with said bovine plasma or serum containing vitronectin;

3) washing said solid support to remove bovine plasma or serum components not bound to the solid support; and
4) recovering the washing from step 3 to obtain vitronectin-free bovine plasma or serum and/or treating the solid support to release the bound vitronectin and recovering the released vitronectin, the monoclonal antibody designated A18 being produced by hybridoma cell line with ECACC accession number 89011103 and the monoclonal antibody designated A27 being produced by hybridoma cell line with ECACC accession number 89011102.

12. The method as claimed in claim 11 in which the monoclonal antibody is A27.

* * * * *

UNITED STATES PATENT AND TRADEMARK OFFICE
CERTIFICATE OF CORRECTION

PATENT NO. : 5,389,518                 Page 1 of 3
DATED : February 14, 1995
INVENTOR(S) : John G. Steele; Patricia A. Underwood It is certified that error appears in the above-indentified patent and that said Letters Patent is hereby corrected as shown below:

On the Title Page, Item 56, References Cited, OTHER PUBLICATIONS, line 12, change "Hayman, E. et al, *Serum Spreading Factor-virtonectin-is present at the Cell Surface and in Tissues* . . ." to -- Hayman, E. et al., *Serum Spreading Factor-vitronectin-is present at the Cell surface and in Tissues* . . . --.

OTHER PUBLICATIONS, lines 18, 19, change "Schakenraad, J. et al., *Kinetics of Cell Spreading on Protein Precoated Substrata: A Study of Interacial Aspects, BIometerials* . . ." to -- Schakenraad, J. et al., *Kinetics of Cell Spreading on Protein Precoated Substrata: A Study of Intefacial Aspects, Biomaterials* . . . --.

Column 1, line 29, change "advantaged" to -- advantageous --.
Column 6, line 5, change "rumour" to -- tumour --.
Column 6, lines 34,35, change "advantaged" to -- advantageous --.
Column 7, line 22, change "run" to -- nm --.
Column 12, line 24, change "at0.1" to -- at 0.1 --.
Column 13, line 9, change "BPLK-21" to -- BHK-21 --.
Column 14, line 53, change "1985," to -- 1985), --.
Column 16, line 11, change "immediatley" to -- immediately --.
Column 17, line 10, change "rumour" to -- tumour --.

UNITED STATES PATENT AND TRADEMARK OFFICE
CERTIFICATE OF CORRECTION

PATENT NO. : 5,389,518

DATED : February 14, 1995

INVENTOR(S) : John G. Steele; Patricia A. Underwood

It is certified that error appears in the above-indentified patent and that said Letters Patent is hereby corrected as shown below:

Column 18, line 8, change "biotehnological" to -- biotechnological --.
Column 18, line 21, change "Monoconal" to -- Monoclonal --.
Column 18, line 56, change "passage" to -- passaged --.
Column 19, line 67, change "non adherent" to -- nonadherent --.
Column 20, line 16, change "blocking'solution" to -- blocking solution --.
Column 20, line 21, change "washedX3" to -- washed X3 --.
Column 20, line 23, change "anti fibronectin" to -- antifibronectin --.
Column 21, line 46, change "fragements" to -- fragments --.
Column 22, line 9, change "wee" to -- were --.
Column 22, line 57, change "war" to -- was --.
Column 22, line 60, change "vaues" to -- values --.
Column 25, line 45, after TABLE 7 insert "Values are OPD absorbances at 450nm corrected for non-specific mouse and rabbit 1gG, and are representative of the amount of VN or FN bound to the surface."
Column 26, line 11, change "1 gG" to -- 1gG --.
Column 26, line 26, before "plastic" delete "on".
Column 26, line 39, change "Mabs" to -- MAbs --.
Column 26, lines 49,57, change "Mab" to -- MAb -- (both occurrences).

UNITED STATES PATENT AND TRADEMARK OFFICE
CERTIFICATE OF CORRECTION

PATENT NO. : 5,389,518

DATED : February 14, 1995

INVENTOR(S) : John G. Steele; Patricia A. Underwood

It is certified that error appears in the above-indentified patent and that said Letters Patent is hereby corrected as shown below:

```
Column 27, line 3, change "Mabs" to -- MAbs --.
Column 27, line 4, change "he cell" to -- the cell --.
Column 27, line 24, change "0" to -- O --.
Column 27, line 43, change "not" to -- no --.
Column 30, line 48, after "coated" delete "is coated".
```

Signed and Sealed this

Twenty-sixth Day of September, 1995

Attest:

BRUCE LEHMAN

*Attesting Officer*   *Commissioner of Patents and Trademarks*